United States Patent [19]
Rava et al.

[11] Patent Number: 5,201,318
[45] Date of Patent: Apr. 13, 1993

[54] CONTOUR MAPPING OF SPECTRAL DIAGNOSTICS

[76] Inventors: Richard P. Rava, 395 Marlborough St., #2R, Boston, Mass. 02115; Rebecca Richards-Kortum, 60 Wadsworth, 16A, Cambridge, Mass. 02142; Michael S. Feld, 56 Hinckley Rd., Waban, Mass. 02168; Joseph J. Baraga, 2922 Fifth Avenue E., Hibbing, Minn. 55746

[21] Appl. No.: 772,620

[22] Filed: Oct. 4, 1991

Related U.S. Application Data

[63] Continuation of Ser. No. 342,311, Apr. 24, 1989, abandoned.

[51] Int. Cl.$^5$ .............................................. A61B 6/00
[52] U.S. Cl. ............................................... 128/665
[58] Field of Search ......................... 128/633, 664, 665

[56] References Cited

U.S. PATENT DOCUMENTS

| | | | |
|---|---|---|---|
| 4,178,917 | 12/1979 | Shapiro | 128/665 |
| 4,449,535 | 5/1984 | Renault | 128/634 |
| 4,479,499 | 10/1984 | Alfano | 128/665 |
| 4,556,057 | 12/1985 | Hiruma et al. | |
| 4,648,892 | 3/1987 | Kittrell et al. | 128/634 |
| 4,768,516 | 9/1988 | Stoddart et al. | |
| 4,785,806 | 11/1988 | Deckelbaum | 128/666 |
| 4,786,813 | 11/1988 | Svanberg et al. | |
| 4,894,547 | 1/1990 | Leffell et al. | 128/633 |
| 4,930,516 | 6/1990 | Alfano et al. | |
| 4,957,114 | 9/1990 | Zeng et al. | |
| 5,003,977 | 4/1991 | Suzuki et al. | 128/633 |
| 5,042,494 | 8/1991 | Alfano et al. | |
| 5,046,501 | 9/1991 | Crilly et al. | |
| 5,062,431 | 11/1991 | Potter et al. | |

OTHER PUBLICATIONS

Pottier et al., Photochemistry & Photobiology, vol. 44, No. 5, pp. 679-687 (1986).
Publication, "Tumour Localization by Means of Laser-Induced Fluorescence in Hematoporphyrin Derivative (HPD) Bearing Tissue".

*Primary Examiner*—William E. Kamm
*Assistant Examiner*—Kevin Pontius
*Attorney, Agent, or Firm*—Hamilton, Brook, Smith & Reynolds

[57] ABSTRACT

The present invention relates to a method of generating and processing spectral information arising from the laser induced fluorescence of tissue. The intensity of fluorescence is recorded as a function of both excitation and emission wavelengths and contour maps of tissue fluorescence are generated which are useful in the diagnosis of condition of the tissue under examination.

20 Claims, 27 Drawing Sheets

CONTOUR MAPPING OF SPECTRAL DIAGNOSTICS

This is a continuation of co-pending application Ser. No. 07/342,311 filed on Apr. 24, 1989, now abandoned.

BACKGROUND

The present invention relates to a system and method for processing spectral information used to aid in the diagnosis of diseased tissue. More particularly, it relates to a method for collecting and displaying the excitation and emission spectra resulting from the laser-induced-fluorescence of tissue.

Methods utilizing the laser-induced-fluorescence ("LIF") of tissue have been developed which permit the characterization of the tissue being examined. This technique has traditionally employed the use of fluorescing agents or dyes which are introduced or applied to the tissue of interest which is then irradiated to induce fluorescence and produce a spectrum that can be used to distinguish diseased from normal tissue. The emission spectra obtained through these methods are normally plotted as intensity versus emission wavelength for a given excitation wavelength. These graphical displays can provide information regarding the diseased condition of tissue as specific peaks in the spectra of abnormal tissue appear which are not present in normal tissue.

Laser catheter systems have also been developed, often in conjunction with known techniques for using fluorescence to aid in diagnosis, for the purpose of inserting a light transmitting device into the human body where laser radiation can be directed onto tissue adjacent the distal end of the catheter to induce fluorescence. The light emitted by the tissue is transmitted along the catheter and analyzed at the proximal end thereof to produce an emission spectrum of the irradiated tissue.

The problem with these standard spectra is that they are highly dependent upon the excitation wavelength that is used such that a highly fragmented view of the spectral characteristics of the tissue is provided. Thus, a more complete method of generating diagnostic information utilizing LIF spectroscopy is needed that more fully characterizes the spectral features of tissue.

SUMMARY OF THE INVENTION

The present invention relates to a system for characterizing tissue fluorescence in the ultraviolet and throughout the visible for the purpose of generating diagnostically useful information. The present system provides the ability to look at fluorescence over a wide range of excitation and emission wavelengths. Such a broad survey is important in fully characterizing the spectroscopic differences between tissue types as well as in aiding in the identification of tissue fluorophores whose presence is correlated with known normal and abnormal states of tissue.

The intensity of fluorescence depends on three parameters: the radiative properties of the fluorophores within the tissue; the wavelength of the exciting light; and the wavelength of the emitted fluorescence. Two types of scans are typically used when recording fluorescence intensity: emission scans (spectra), in which the excitation wavelength is held constant and the emission wavelength is varied, and excitation scans (spectra), in which the emission wavelength is constant and the excitation is varied. Either type of scan alone contains useful information about the tissue constituents; however, both excitation and emission profiles are needed for a full characterization of fluorescence. In fact, a complete fluorescence characterization involves recording the fluorescence intensity for each possible pair of excitation and emission wavelengths.

Typically, emission (or excitation) scans are presented as two dimensional plots with emission (or excitation) wavelengths running along one axis and fluorescence intensity running along the other axis. In order to display intensity for each possible pair of excitation and emission wavelengths, a 3-dimensional plot of intensity vs. excitation and emission is one alternative for displaying the information for analysis. There are also two methods employed for representing such plots in two dimensions: perspective drawing and contour (topographic) mapping. In a preferred embodiment, contour maps are employed to display the data as they provide for viewing many of the important features on one plot.

This method is employed in conjunction with laser catheter systems used to induce fluorescence in bodily tissue both in vitro and in vivo without the use of fluorescence enhancing agents, also referred to herein as "autofluorescence". The procedure is illustrated using data collected on excised tissue samples, including artery wall, gastrointestinal tissue and bladder tissue, but are usefully applied to all types of tissue and the abnormal or diseased conditions which can be differentiated by optical characteristics.

In particular, fluorophores present in the tissue under study, whose concentration varies with the condition of the tissue, have been associated with specific features of the contour spectra. This correlation between the contour spectra and the chemical constituents of the tissue is useful in the construction of diagnostic methods which can systematically differentiate tissue type and condition.

The above and other features of the invention, including various novel details in the methods described and certain combinations thereof, will now be more particularly described with reference to the accompanying drawings and pointed out in the claims. It will be understood that the particular methods of diagnosis embodying the invention are shown by way of illustration only and not as a limitation of the invention. The principle features of the invention may be employed in various embodiments without departing from the scope of the invention.

BRIEF DESCRIPTION OF THE DRAWINGS

FIGS. 21a and 21b show average contour maps on two different scales of bladder tumor.

DETAILED DESCRIPTION OF THE INVENTION

Figure 1:
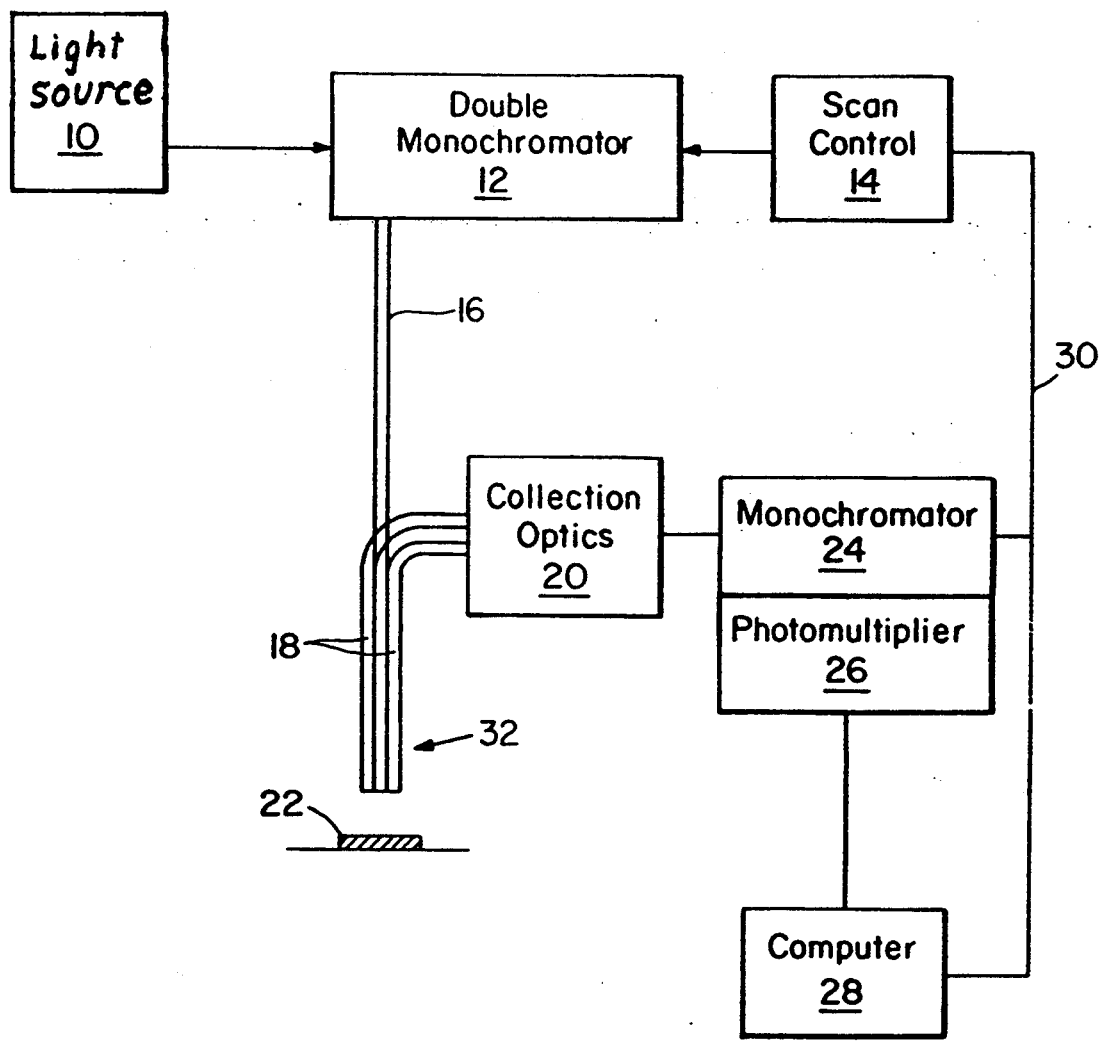
FIG. 1 is a schematic diagram of an apparatus used in conjunction with the present invention.

FIG. 1 illustrates a preferred embodiment of the system that is used in generating and processing matrices of fluorescence intensity obtained as a function of both excitation and emission wavelengths. Light source 10 can be a broadband source such as a Xenon arc lamp. However, a tunable laser can also be employed to provide excitation radiation of variable wavelength. A double monochromator 12 subject to scan control 14 directs radiation of selected wavelength through optical fiber 16 onto the tissue sample 22. Collection fibers 18 collect the fluorescent radiation emitted by the sample 22 and direct it through collection optics 20 and into a second double monochromator 24. Photomultiplier 26 then detects the radiation and generates a signal that is forwarded to computer 28 for processing and display. Computer 28, via line 30, can be used to control the scanning parameters of the two monochromators 12 and 24.

The optical probe or catheter 32 can also be used in vivo within the human body to perform diagnostic scans on living tissue. The methods of the present invention may be used in conjunction with the laser catheter systems disclosed in U.S. Pat. No. 4,718,417, incorporated herein by reference.

Fluorescence intensity from normal aorta was recorded over a range of from 250 to 700 nm every 5 nm for both excitation and emission. The system used for this type of measurement is easily tuned over a large range of excitations. The system can use a rhodamine solution as a reference, so that differences in intensity of the exciting light at different wavelengths are automatically removed from the spectra. This makes it possible to obtain fluorescence intensities over a large range of excitations and emissions on a single sample of tissue in a reasonable amount of time. Gratings blazed at 250 nm have been used so that emission spectra can be taken from 250 to 700 nm.

To generate the data, emission scans were taken with excitations of 250 to 500 nm every 5 nm. The emission ranges ran from the excitation +12.5 nm to 697.5 nm every 5 nm. The FIGURES described below are generated by sequential acquisition of emission scans; however, excitation scans could be used as well to display the relationship between excitation and emission. The FWHM (full width-half maximum) of the excitation source was 2 nm, and the emission FWHM was 3 nm. An integration time of 1 second at each point yielded a reasonable signal to noise ratio for all scans.

Figure 2:
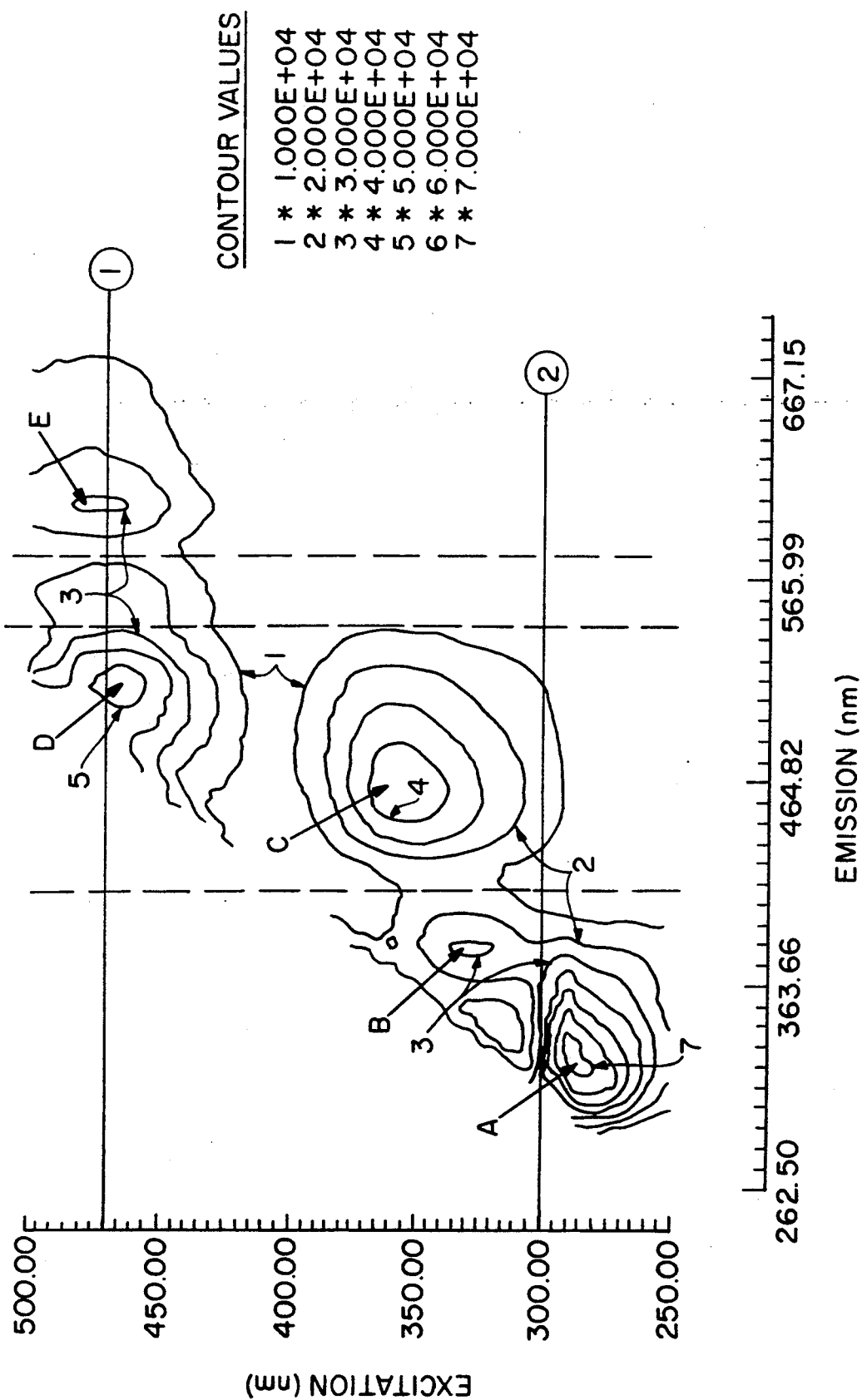
FIG. 2 illustrates a contour map of morphologically normal aorta.

FIG. 2 shows the contour map that was generated from a sample of morphologically normal aorta. The map shows five distinct peaks (labeled A–E in FIG. 2). Each peak potentially represents a distinct fluorophore; however, it is known that fluorescence reabsorption in the tissue can create artificial peaks in emission spectra. On the contour map, such reabsorption valleys should appear as depressions at constant emission wavelength, since the wavelength of reabsorption does not depend on excitation. The three dashed vertical lines in FIG. 2 are examples of such reabsorption. The two lines near 570 nm emission represent absorption due to oxy-hemoglobin, while the line near 415 nm is the Soret band of heme. Based on this interpretation, the two peaks D and E are due to a single fluorophore which is known to be elastin/collagen. The peaks B and C may also be due to a single fluorophore, although the fact that they are slightly shifted in excitation from one another supports the notion that the peaks are due to two distinct fluorophores.

Figure 3A:
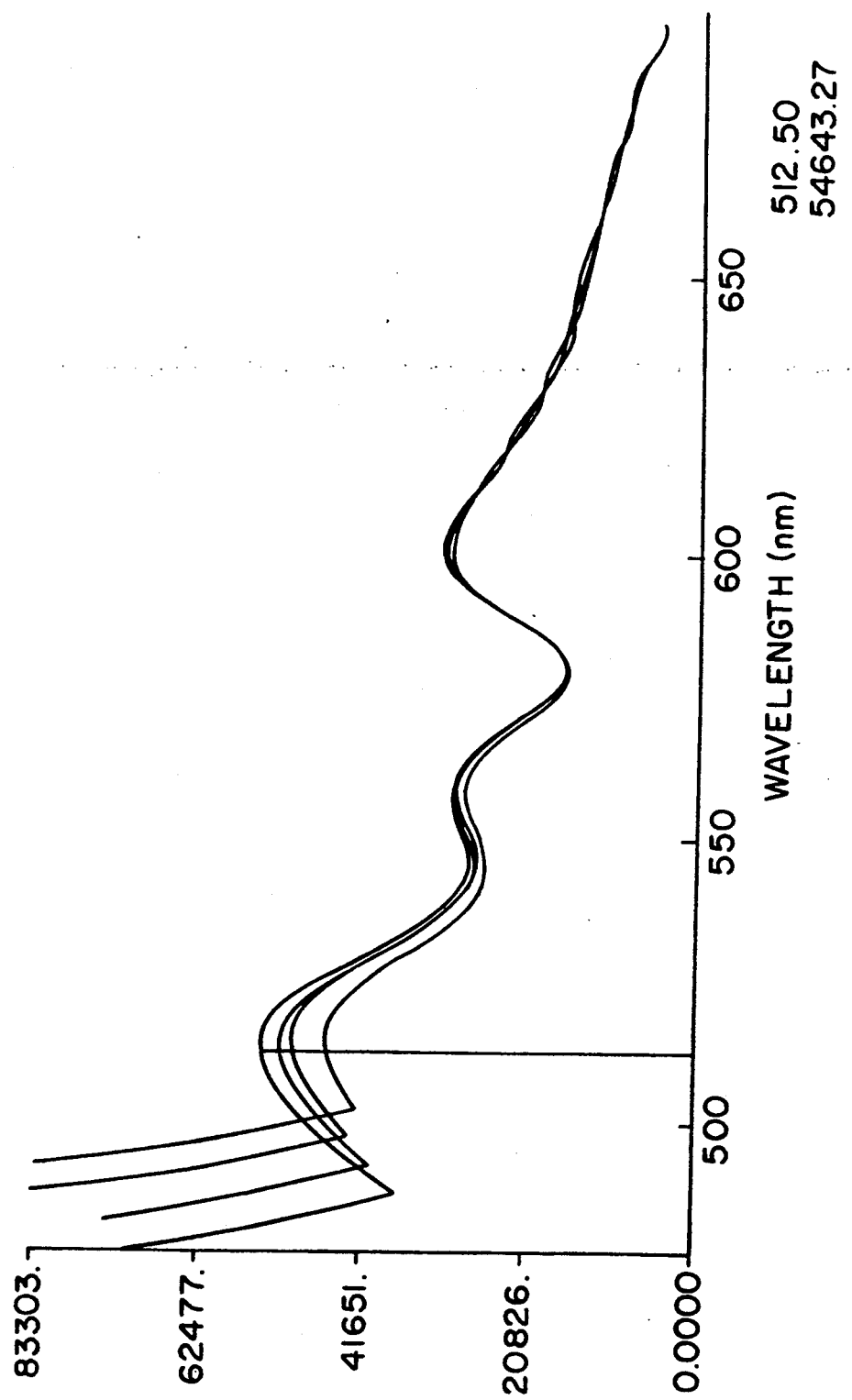
FIG. 3a presents four emission scans from the region about line A-B of FIG. 2.

Horizontal lines, that is, lines of constant excitation, on the map represent emission scans. Four emission scans from the region designated by line A–B in FIG. 2 are shown in FIG. 3a. These scans are very similar to those with 476 nm excitation. The two peaks at 560 and 600 nm are artificial in that they are created by the reabsorption valleys at 540 and 580 nm, as was surmised from the contour map.

Figure 3B:
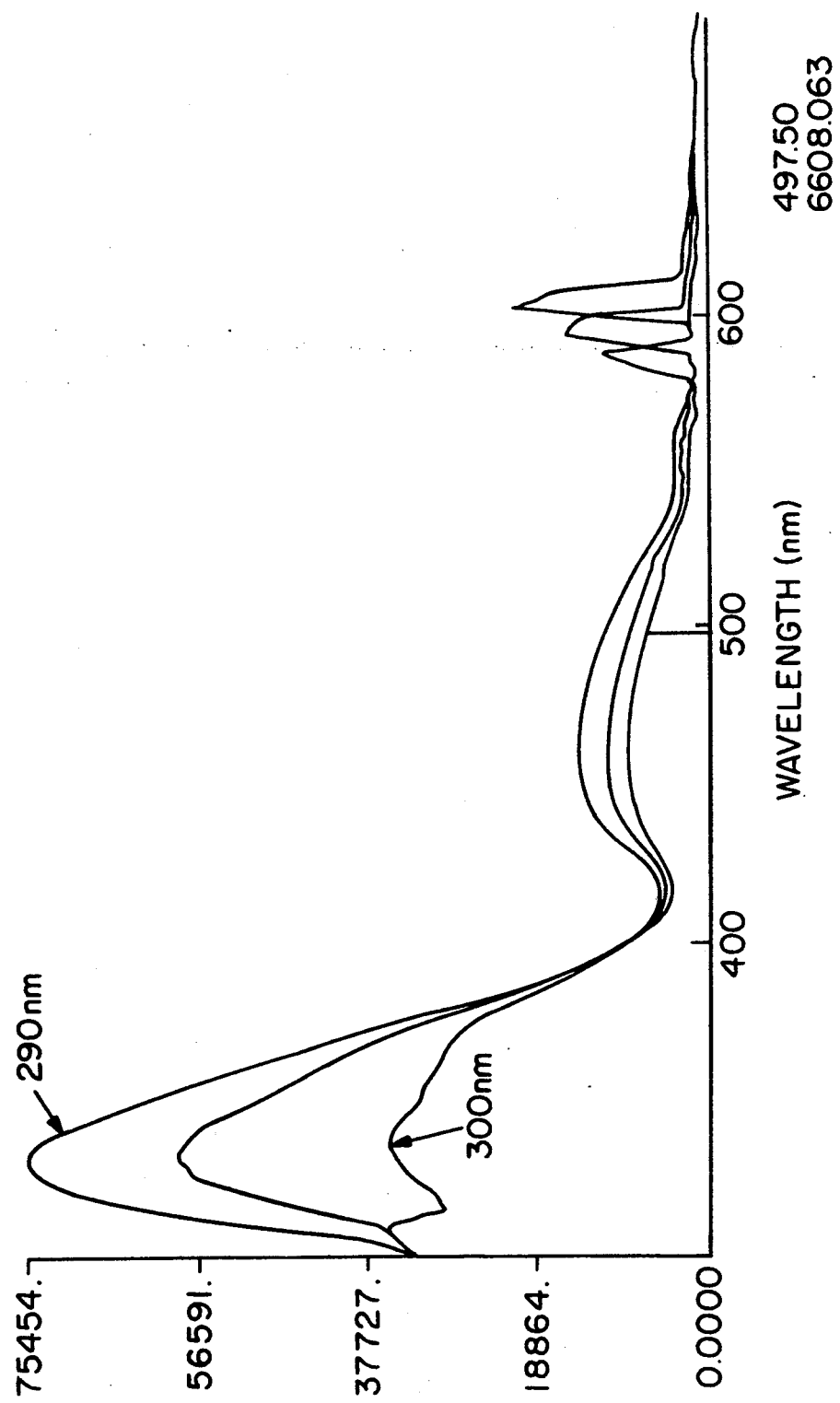
FIG. 3b presents emission scans from line A-C in FIG. 2.

Emission scans from line A–C are shown in FIG. 3b. As can be seen from the contour map, the intensity of fluorophore A, emitting at 340 nm, is strongly dependent on excitation wavelength near 300 nm. This is vident from the very close spacing of the contour lines in this region. This fluorophore has been identified as tryptophan. The Soret valley at 415 nm is also seen in these emission scans, as is the emergence of another peak (B) at 390 nm, as excitation wavelength is made longer. Based on spectra from thin samples of artery, peak C (at 450 nm emission) was assumed to be artificially created by the Soret valley, so that peaks B and C were assigned to a single fluorophore. However, as the contour map reveals, these peaks occur at slightly different excitations, and it is possible that two distinct fluorophores are being observed.

This system has been used to determine optimal excitation and emission wavelengths for differentiating normal and atherosclerotic aorta. Also, contour maps of fibrous, fatty and calcified plaques have been constructed. By normalizing these maps and then subtracting them from, or ratioing them, to a normalized map of normal aorta, excitation and emission wavelengths at which fluorescence lineshapes of normal and diseased tissue are most different can be easily identified.

FIGS. 4–7 present data collected as excitation-emission matrices (EEM's) of bulk samples of normal and pathological human aorta tissue. This data, which is presented in the form of contour maps as well as perspective drawings is used to determine an optimum wavelength for distinguishing between normal and pathological tissue.

Tissue samples are classified as either normal, fibrous, fatty, or calcified. In all, there were nine normal samples run from five different patients six calcified samples which were all from the same patient, eight fibrous samples taken from four different patients, and two samples of fatty tissue from the same patient.

Figure 7A:
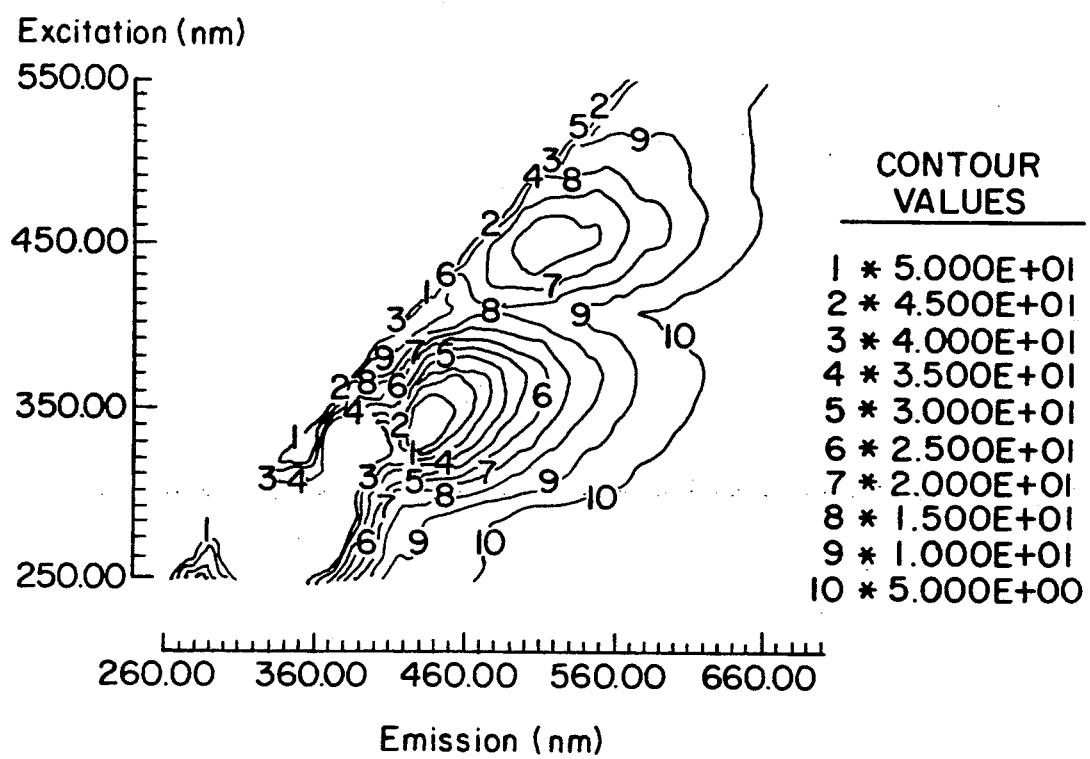
FIGS. 7a and 7b show a contour map and a perspective view, respectively, of an excitation-emission matrix of fatty aortic tissue.
Figure 7B:
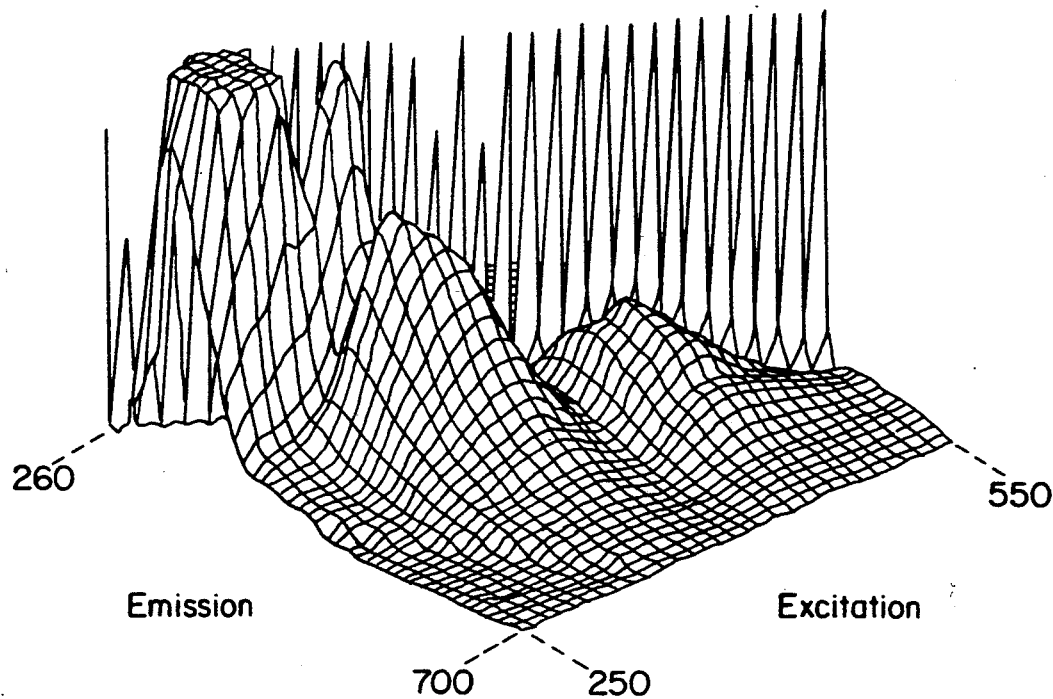

The EEM's of each tissue type were averaged with the exception of the fatty sample shown in FIG. 7

Figure 4A:
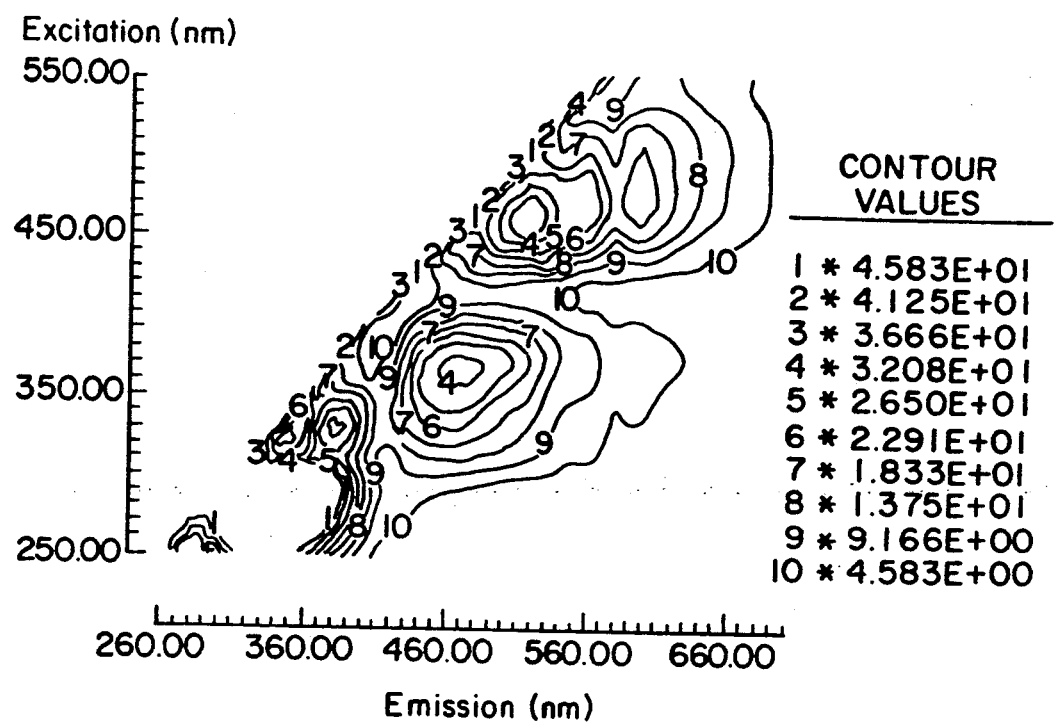
FIGS. 4a and 4b present a contour map and a perspective view of an excitation emission matrix of fluorescence intensity of normal aorta.
Figure 4B:
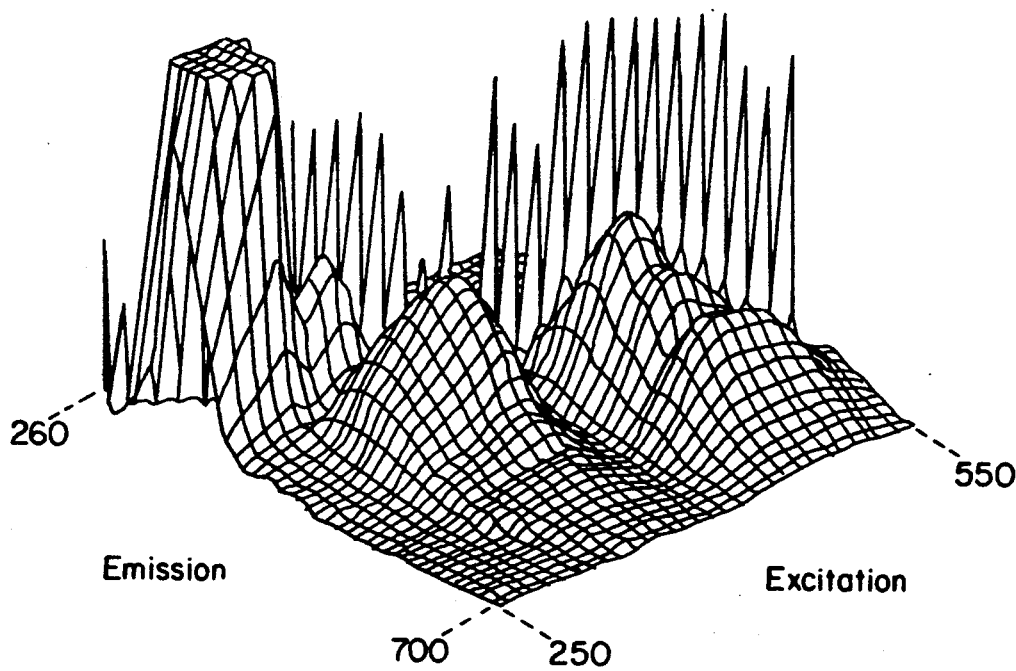
Figure 5A:
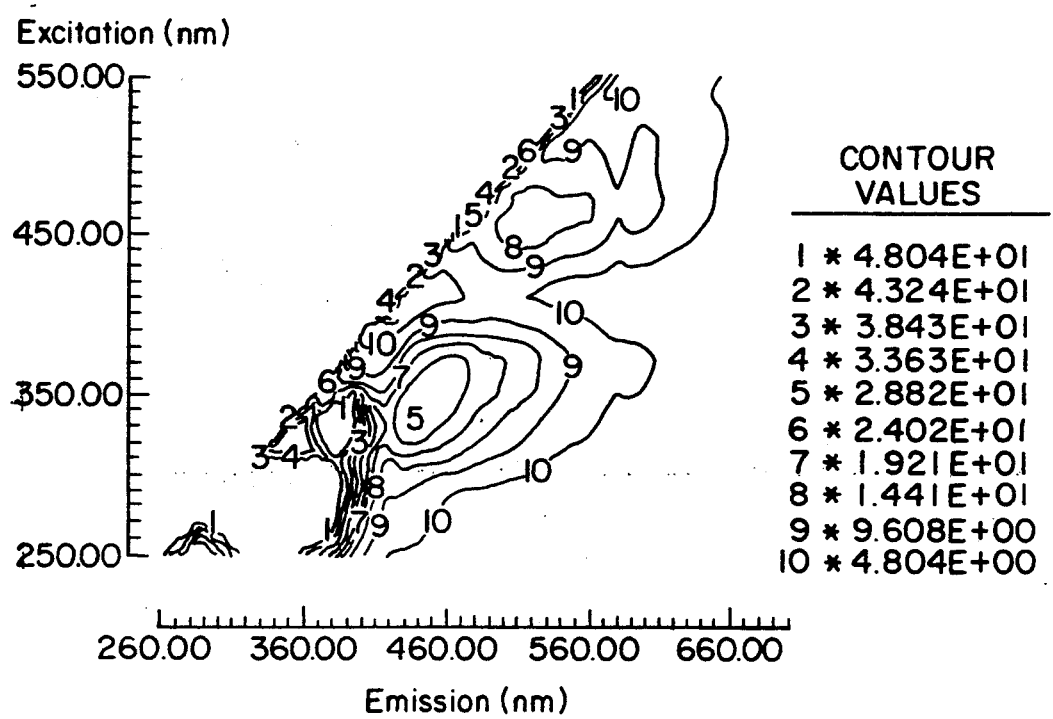
FIGS. 5a and 5b show a contour map and a perspective view, respectively, of an averaged excitation-emission matrix of fibrous aortic tissue.
Figure 5B:
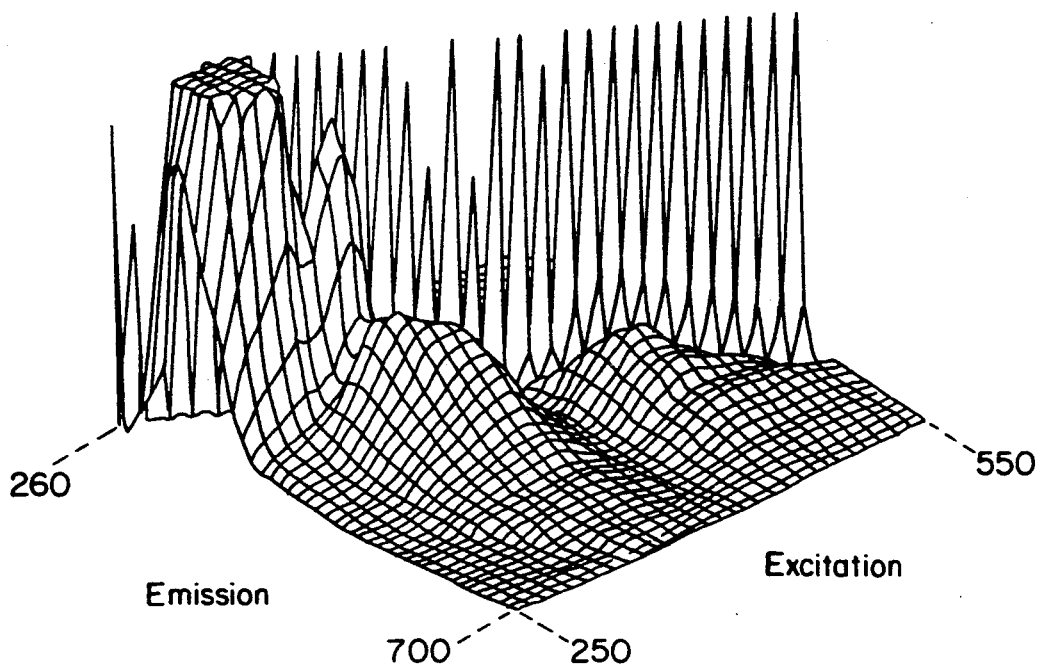
Figure 6A:
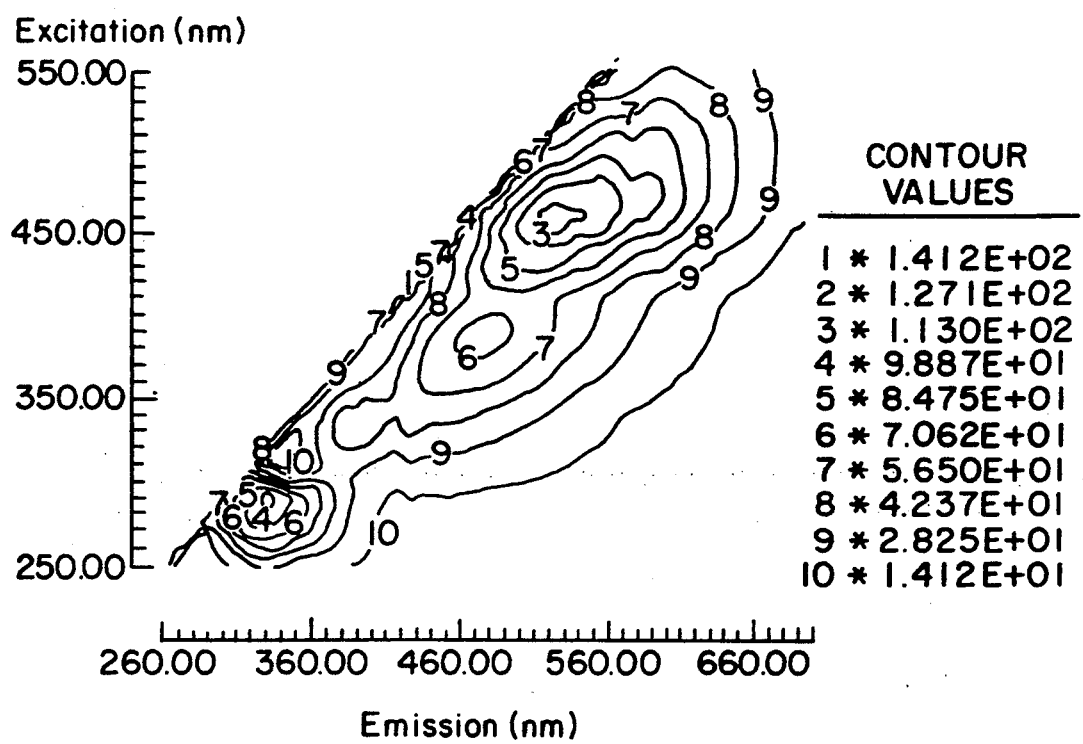
FIGS. 6a and 6b show a contour map and a perspective view, respectively, of an averaged excitation-emission matrix of calcified aortic tissue.
Figure 6B:
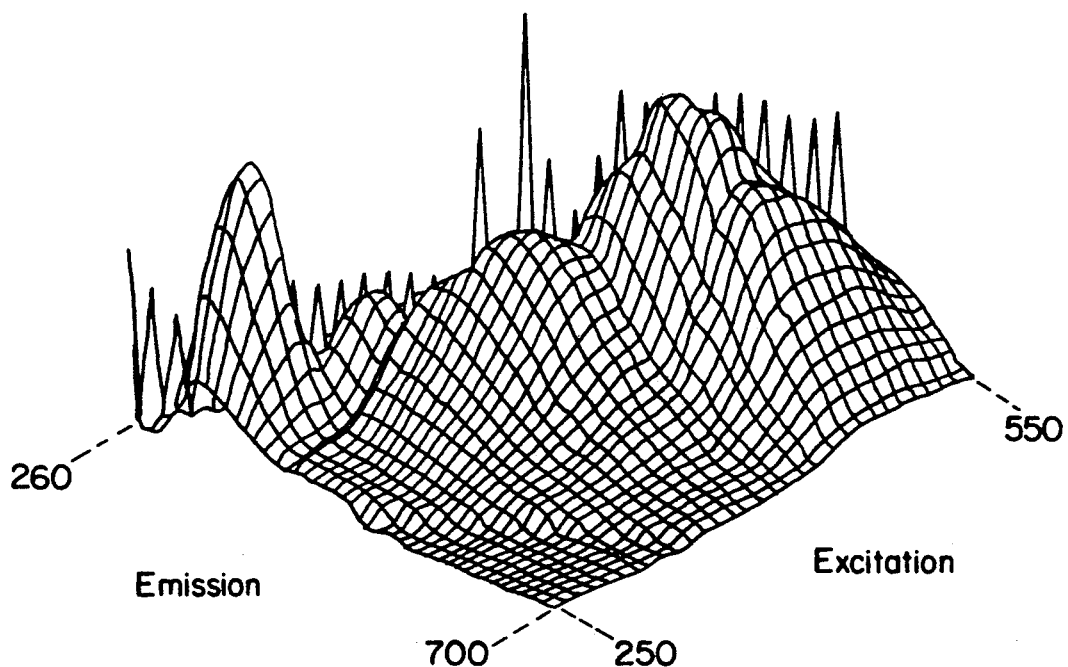

The main features of the EEM's of the normal samples of FIGS. 4a and 4b are the dominant tryptophan peak in the uv and the absorption valleys at 415 nm, which are believed to be caused by the presence of hemoglobin in the tissue. There is also weaker fluorescence in the visible range, which is primarily due to chromophores within the collagen and elastin. The most noticeable difference between the EEM's of the normal and fibrous tissue (at FIGS. 5a and 5b) is that there is greater fluorescence at the longer wavelengths in normal compared to fibrous. There also appears to be a difference in the location of the peak of the fluorescence due to chromophores within the collagen, but this may be the result of less hemoglobin absorption in the fibrous tissue. One difference between the calcified tissue shown in FIGS. 6a and 6b and the normal tissue is that the fluorescence peak due to tryptophan is about a factor of two lower in the calcified tissue. In addition, the fluorescence due to chromophores within the collagen and elastin is two to three times greater in the calcified tissue, and there is also less absorption at 415 nm. One of the chromophores found within the collagen or elastin morphologic structures is pyridinoline which is known to fluoresce in the range 400–420 nm when excited by radiation in the range of 360–370 nm.

Figure 8A:
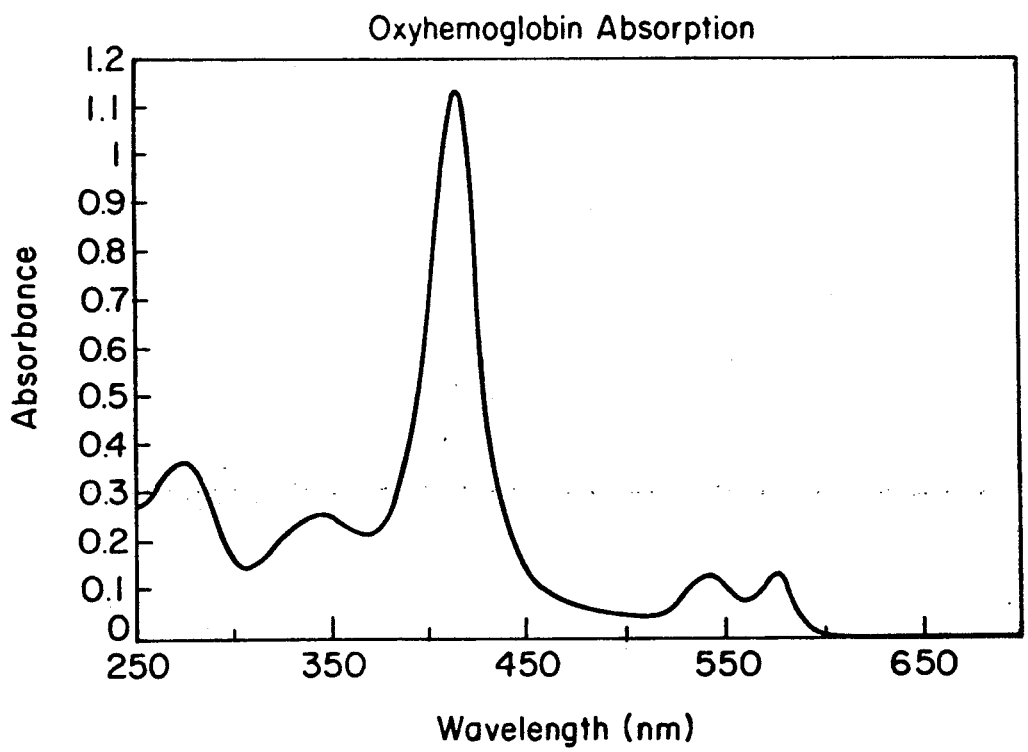
FIGS. 8a and 8b show an absorption spectrum and a contour map, respectively, of hemoglobin.
Figure 8B:
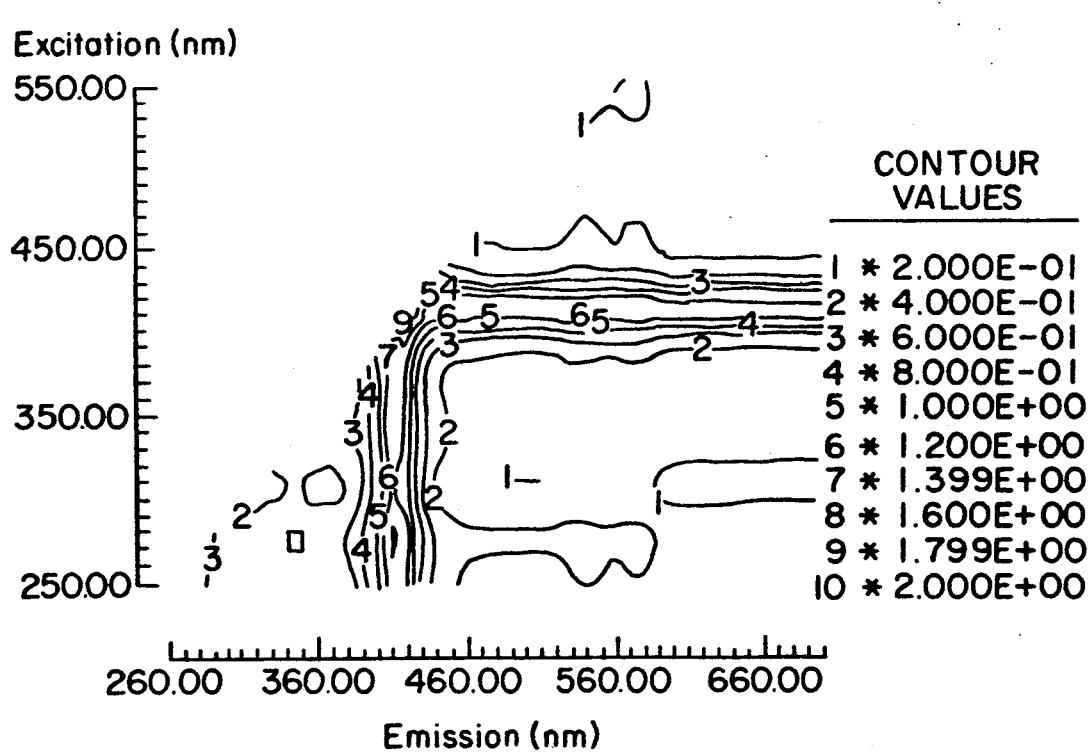
Figure 9A:
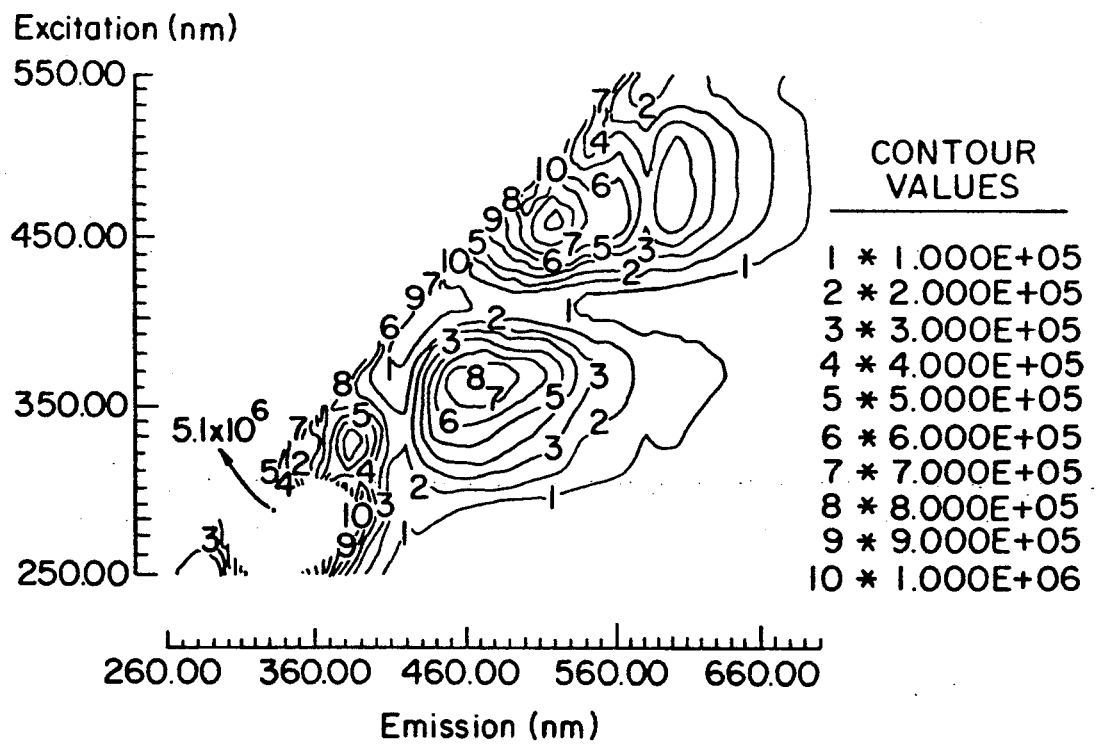
FIGS. 9a and 9b show contour maps of bulk aorta before and after the sample is soaked in saline.
Figure 9B:
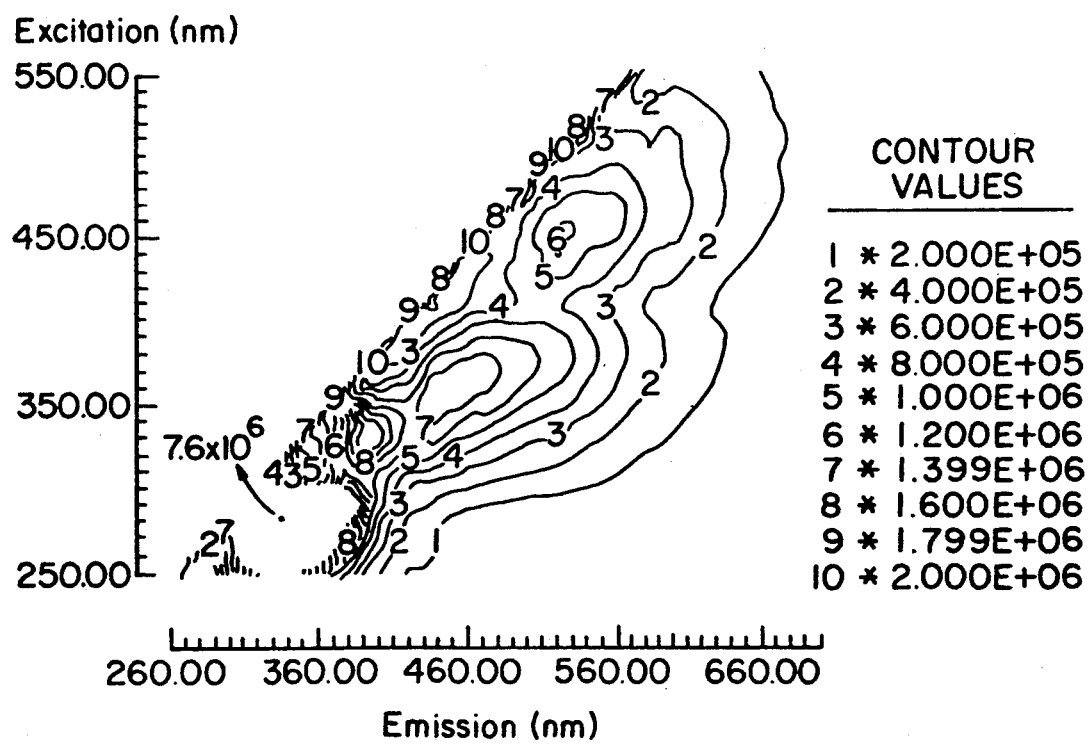

Hemoglobin (Hb) plays an important role in in vitro aorta EEM's. The large Soret absorption band at 416 nm is responsible for the deep valleys seen in the contour map both at excitations and emissions around 416 nm. Oxyhemoglobin also produces the minor valleys near 540 and 580 nm. Note that heme is one of the chromophores found in hemoglobin. Heme has an absorption region centered around 560 nm. This conclusion is supported by the following observations:

1) The absorption spectrum of hemoglobin has peaks coincident with the valleys mentioned above (FIGS. 8a and 8b).
2) In vitro aorta samples have typically been exposed to lysed red blood cells and, therefore, free Hb which can readily diffuse into the tissue.
3) These valleys are absent in 10 μm sections of intima and media. The effects of absorption on LIF are negligible in these thin sections.
4) These valleys can be nearly eliminated by soaking an in vitro bulk aorta sample in saline before collecting the spectra (FIGS. 9a and 9b). This soaking removes most of the Hb, which can freely diffuse from the tissue.

Figure 10:
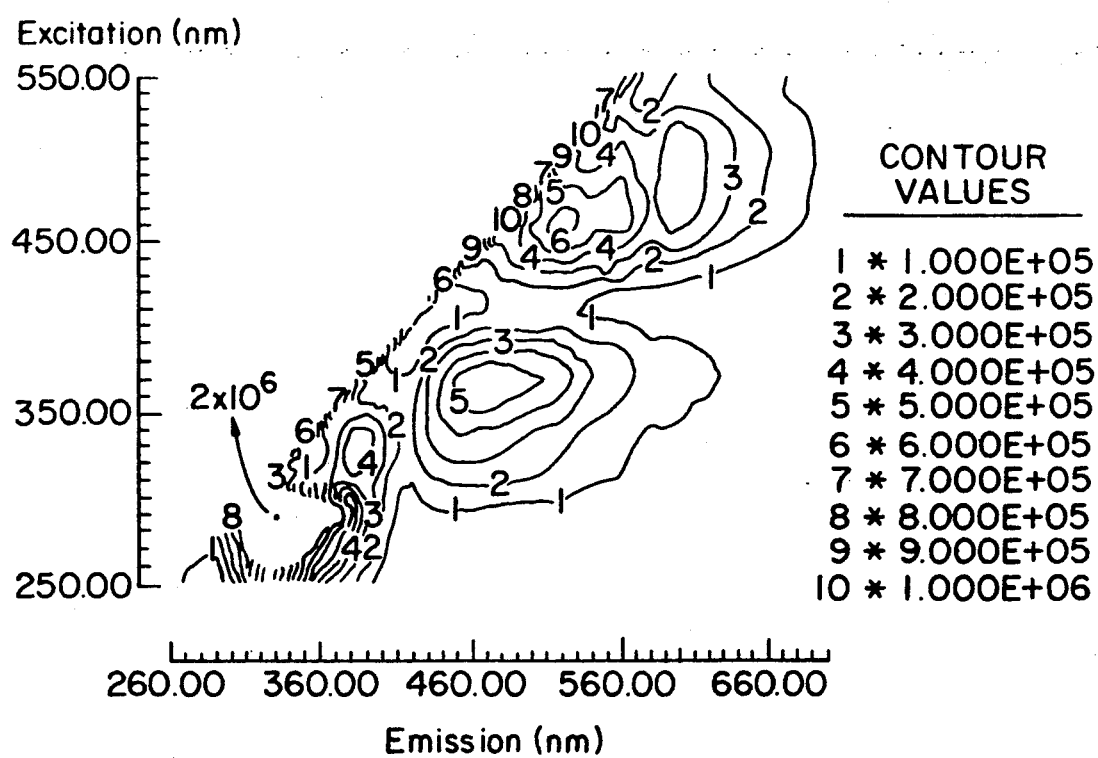
FIG. 10 shows a contour map of the attenuation matrix of hemoglobin.

The physical basis for these valleys is quite simple: a portion of the incident excitation light as well as the emitted fluorescence is reabsorbed by the Hb, causing a reduction in the fluorescence intensity. This can be clearly seen from the single layer tissue fluorescence model, in which the observed fluorescence intensity $S(\lambda_x,\lambda_m)$ can be written $$S(\lambda_x, \lambda_m) = \frac{kF(\lambda_x, \lambda_m)}{x_{Hb}A_{Hb}(\lambda_x, \lambda_m) + x_{SP}A_{SP}(\lambda_x, \lambda_m)} \qquad (1)$$

where $F(\lambda_x,\lambda_m)$ is the "intrinsic" tissue fluorescence, i.e. the tissue fluorescence from a thin section, free of absorption effects; $x_{Hb}A_{Hb}(\lambda_x,\lambda_m) = \mu_{Hb}(\lambda_x) + \mu_{Hb}(\lambda_m)$, where $A_{Hb}$ represents the attenuation spectrum of Hb (and similarly for SP, where SP refers to fixed tissue absorbers). $A_{Hb}(\lambda_x,\lambda_m)$ can be thought of as the normalized attenuation matrix of Hb, with $x_{Hb}$ representing its concentration; it can be generated from the Hb absorption spectrum if effects of scattering are neglected. A contour map of $A_{Hb}(\lambda_x,\lambda_m)$, which clearly shows the Soret absorption bands, is shown in FIG. 10.

Figure 11A:
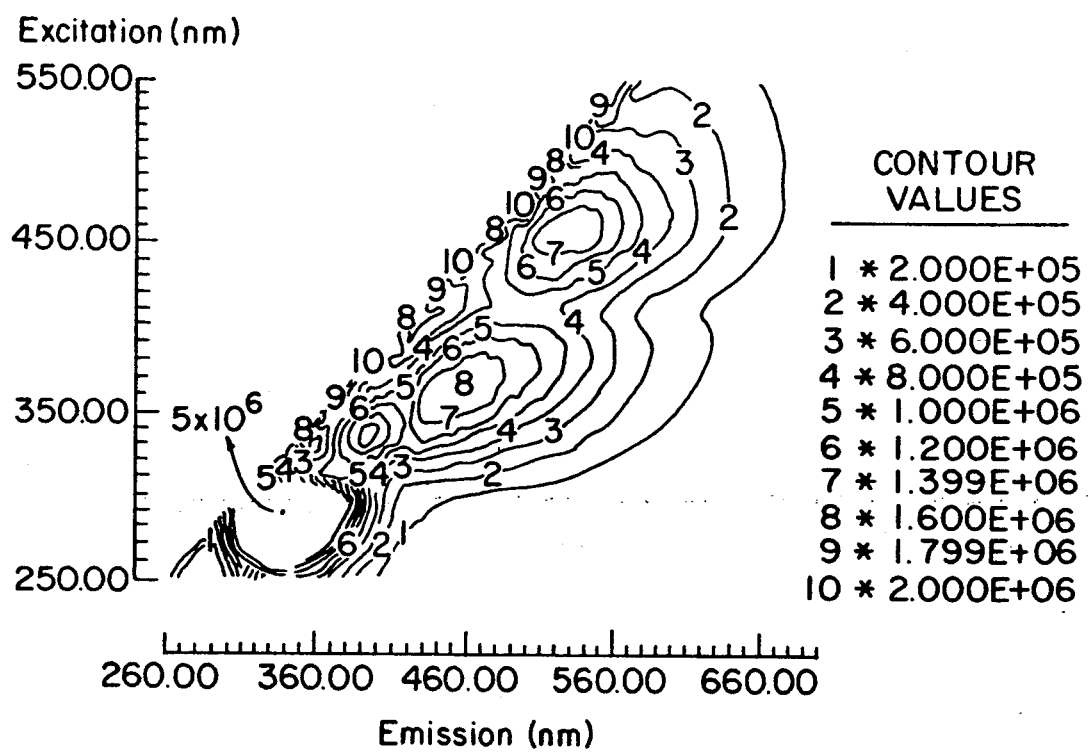
FIGS. 11a and 11b show contour maps of aortic tissue after soaking to remove hemoglobin, and after the addition of the effects of hemoglobin using the hemoglobin absorption matrix.
Figure 11B:
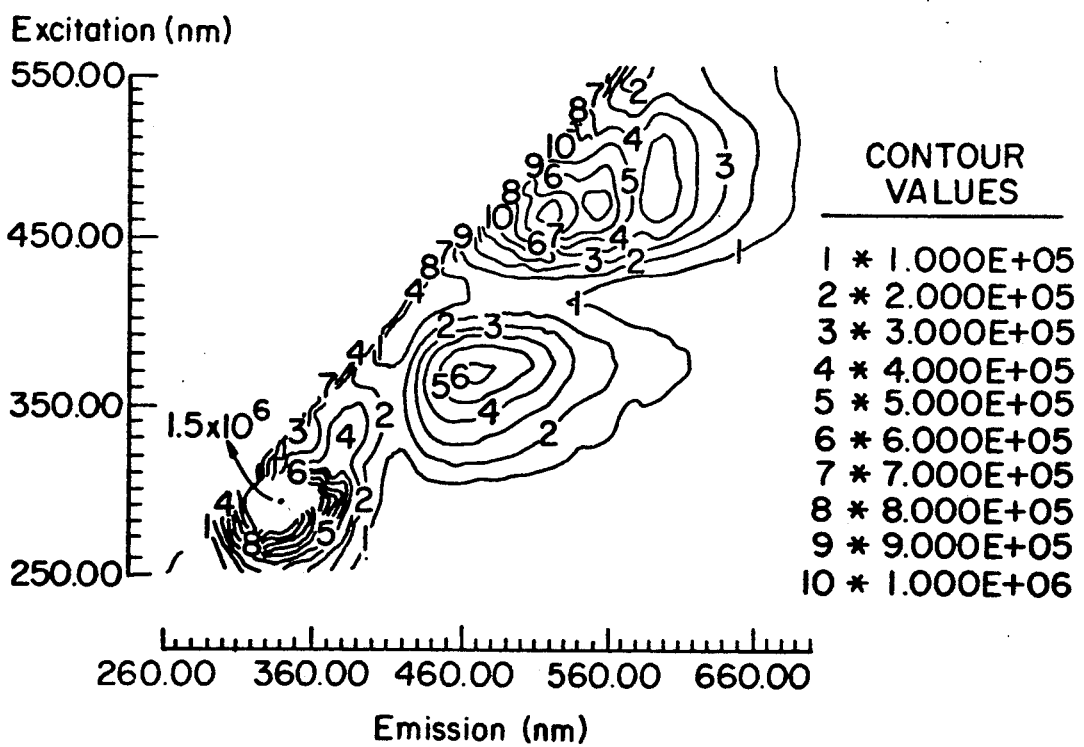

Equation (1) can be rewritten $$S(\lambda_x, \lambda_m) = \frac{x_{SP}A_{SP}S_0(\lambda_x, \lambda_m)}{x_{Hb}A_{Hb}(\lambda_x, \lambda_m) + x_{SP}A_{SP}}$$

where $S_0(\lambda_x,\lambda_m)$ is the fluorescence observed in the absence of Hb($x_{Hb}=0$). By making the crude assumption that $A_{SP}$ is a constant (not dependent on wavelength) over the entire EEM, by using values of $x_{Hb}$ and $x_{SP}A_{SP}$ determined with 476 nm excitation, and by using the calculated Hb absorption matrix, the effect of Hb absorption can be reproduced from the soaked aorta EEM ($x_{Hb}=0$) by "dividing" Hb absorption matrix into it in the manner specified by Eq. 2. The result is displayed in FIGS. 11a and 11b. The structure of the aorta EEM with Hb (before soaking) is recovered, although peak intensities, especially in the ultraviolet, are smaller than in the actual EEM.

Using this method, Hb absorption effects can also be produced in an ex vivo aorta sample. The EEM of the ex vivo sample which has presumably not been exposed to free Hb, is quite similar to that of the soaked aorta. By dividing the Hb absorption matrix into it in the manner of Eq. 2, an EEM very similar to that of Hb-containing in vitro aorta is produced.

This method of correcting for the presence of absorbers within the tissue being examined can be applied to other absorbing components. The removal of the effects of absorption can assist in providing a clearer spectrum in which all of the avisibile information regarding tissue fluorescence can be recovered.

Figure 12:
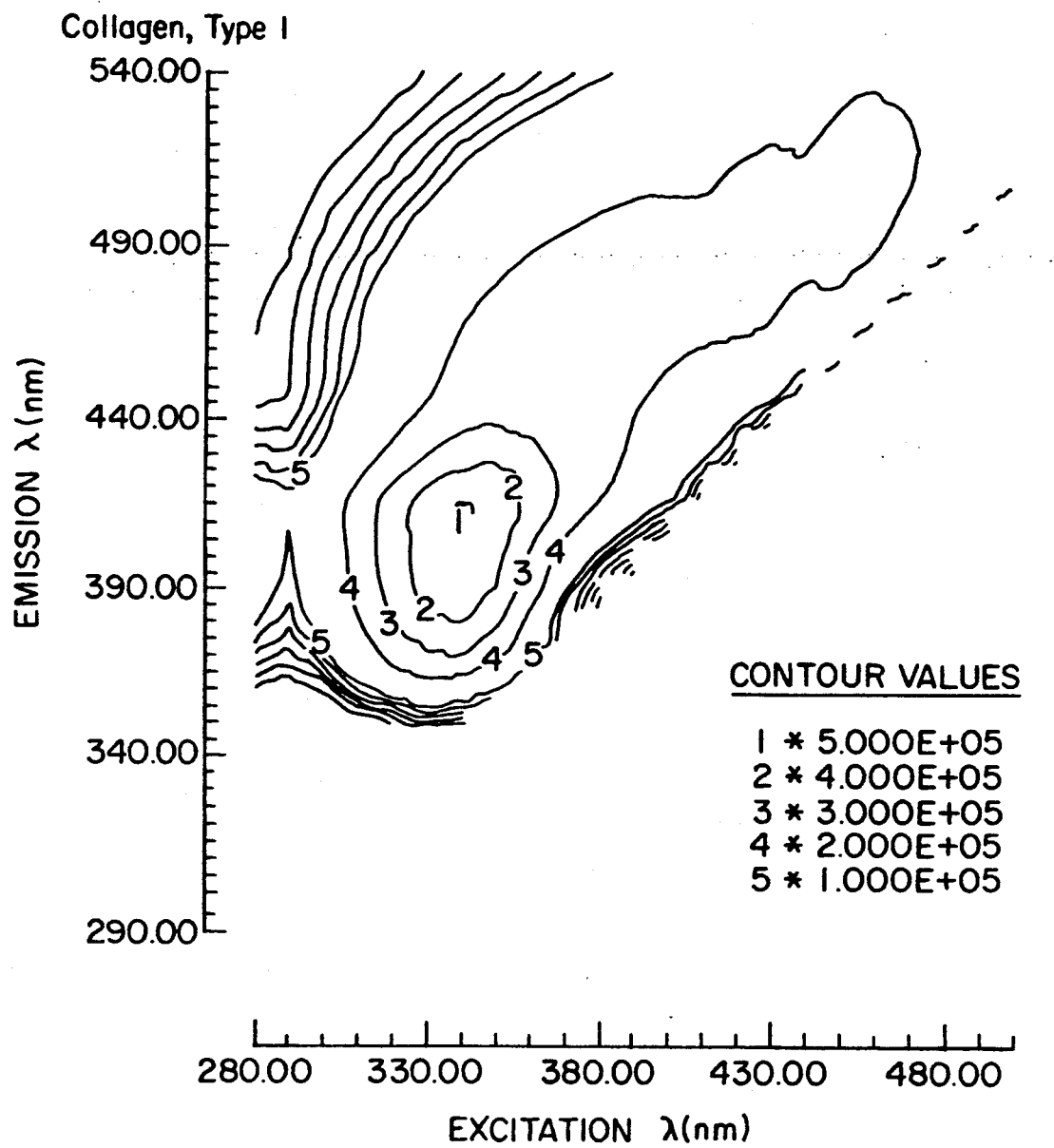
FIG. 12 illustrates a contour 12 of powdered type 1 bovine collagen.

The system also assists in identifying the chromophores which contribute to arterial tissue fluorescence spectra. Contour maps provide very useful insight about the number and nature of tissue chromophores. To separate contributions from different chromophores, maps can be obtained from thin tissue sections, which contain a limited number of chromophores (e.g. ceroid in necrotic core) and are free of reabsorption effects. Also maps of pure compounds, which are suspected tissue chromophores, can be constructed for comparison with tissue maps. For example, FIG. 12 contains a map of powdered type 1 bovine collagen. Other components studied include chromophores or structures containing chromophores such as elastin, tryptophan, hemoglobin and flavoprotein.

Although type 1 collagen has emission in the same region as does normal aorta, there are several important differences. Some of these are due to reabsorption of hemoglobin; the collagen map does not show valleys at 420, 540 and 580 nm. However, other differences are not related to reabsorption, and indicate that tissue fluorescence in this region contains contributions from chromophores other than those present in type 1 collagen.

The methods of the present invention have been used to differentiate normal and pathologic tissues in human colon and urinary bladder with excitation wavelengths ranging from 250-500 nm, utilizing fluorescence contour maps. This contour mapping serves to identify optimal excitation wavelengths for differentiating normal and pathologic tissue fluorescence spectra and to identify tissue chromophores contributing to the fluorescence of normal and pathologic tissues.

Fluorescence contour maps were collected from 18 colon specimens and 15 urinary bladder specimens. Fluorescence contour maps were constructed from a series of fluorescence emission spectra recorded using a spectrofluorimeter. Excitation wavelengths were varied in 10 nm steps from 250 to 500 nm. Fluorescence was collected at 5 nm intervals from $\lambda exc+10$ nm to $2\lambda exc-10$ nm. Incident beam size was $\sim 2\times 3$ mm, smaller than the surface area of all tissue samples, thus absolute intensity information has been preserved in the analysis of this data. To correct for day to day variations in the spectrofluorimeter alignment, all data has been divided by a fluorescence intensity standard which is run each day. Emission gratings were blazed at 250 nm. All data presented here has been corrected for the non-uniform spectral response of the collection system.

The following method of data analysis was employed for both colon and bladder tissues. An average normal contour map $N_A(\lambda_x,\lambda_m)$, and an average pathologic contour map $P_A(\lambda_x,\lambda_m)$ were calculated and were plotted on a log scale with contours ranging from 50 to 0.5. To compare contour maps of normal and pathologic tissues, a ratio of the average contour maps was constructed as:

$$R_A(\lambda_x, \lambda_m) = \frac{P_A(\lambda_x, \lambda_m)}{N_A(\lambda_x, \lambda_m)}$$

and was plotted on a linear scale with contours varying from 2.0 to 0.2. Here, a contour at 1.0 indicates regions in which the fluorescence emission from normal and pathologic tissues is the same, while contours at values greater (less) than 1.0 indicate regions where the emission from pathologic tissue is greater (less) than that from normal tissues Regions of greatest difference in the fluorescence spectra of normal and pathologic tissues were assessed from this average ratio map. This information was used in defining a process for determination of tissue type.

To assess how the variability of individual tissues affected this comparison, the following ratio maps were constructed for each individual normal and pathologic sample:

$$R_N(\lambda_x, \lambda_m) = \frac{N(\lambda_x, \lambda_m)}{N_A(\lambda_x, \lambda_m)} \; ; R_P(\lambda_x, \lambda_m) = \frac{P(\lambda_x, \lambda_m)}{N_A(\lambda_x, \lambda_m)}$$

Data from these individual ratio maps was used to test processes suggested in the above data analysis procedure.

Figure 13A:
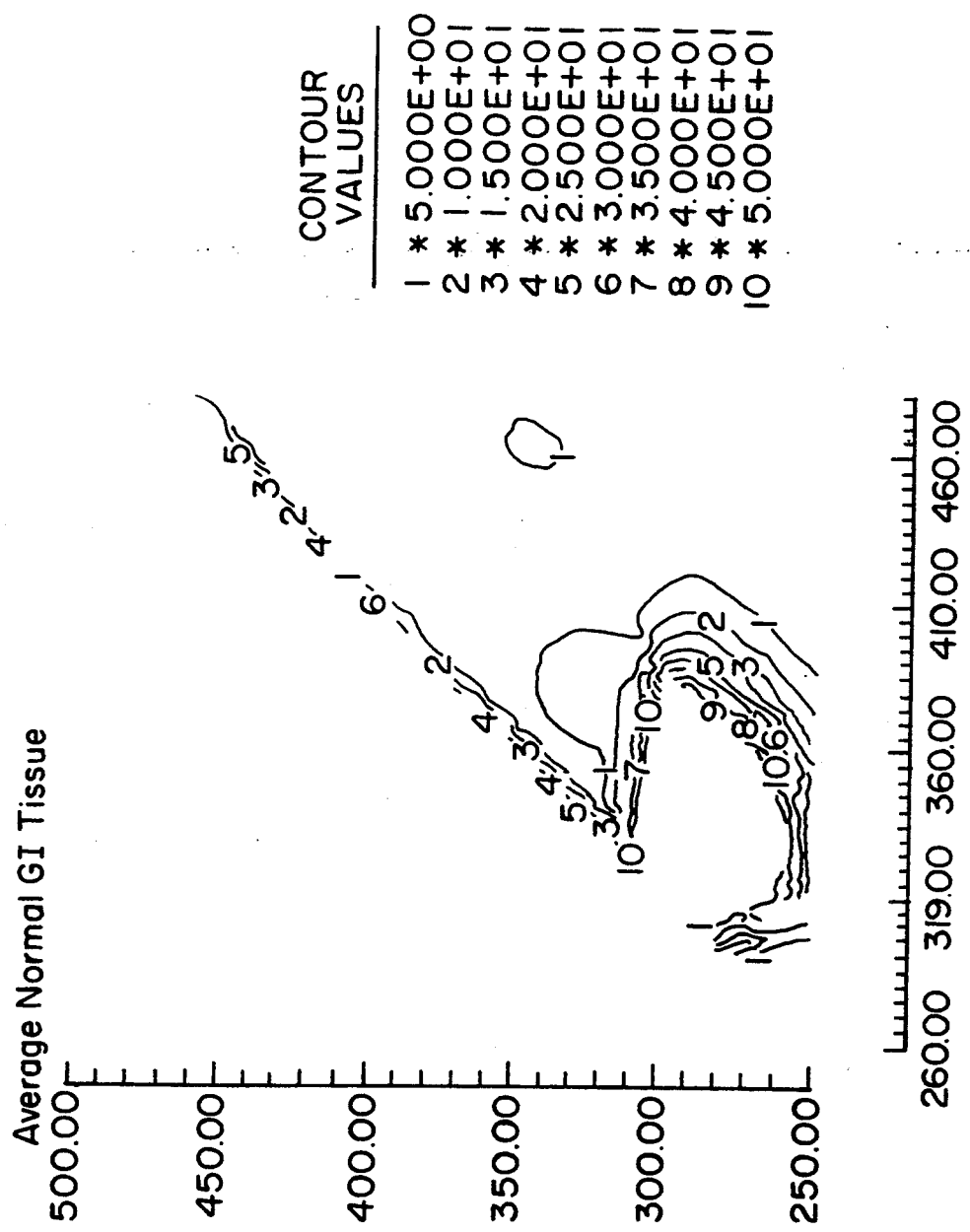
FIGS. 13a and 13b show average fluorescence contour maps of normal human colon tissue.
Figure 13B:
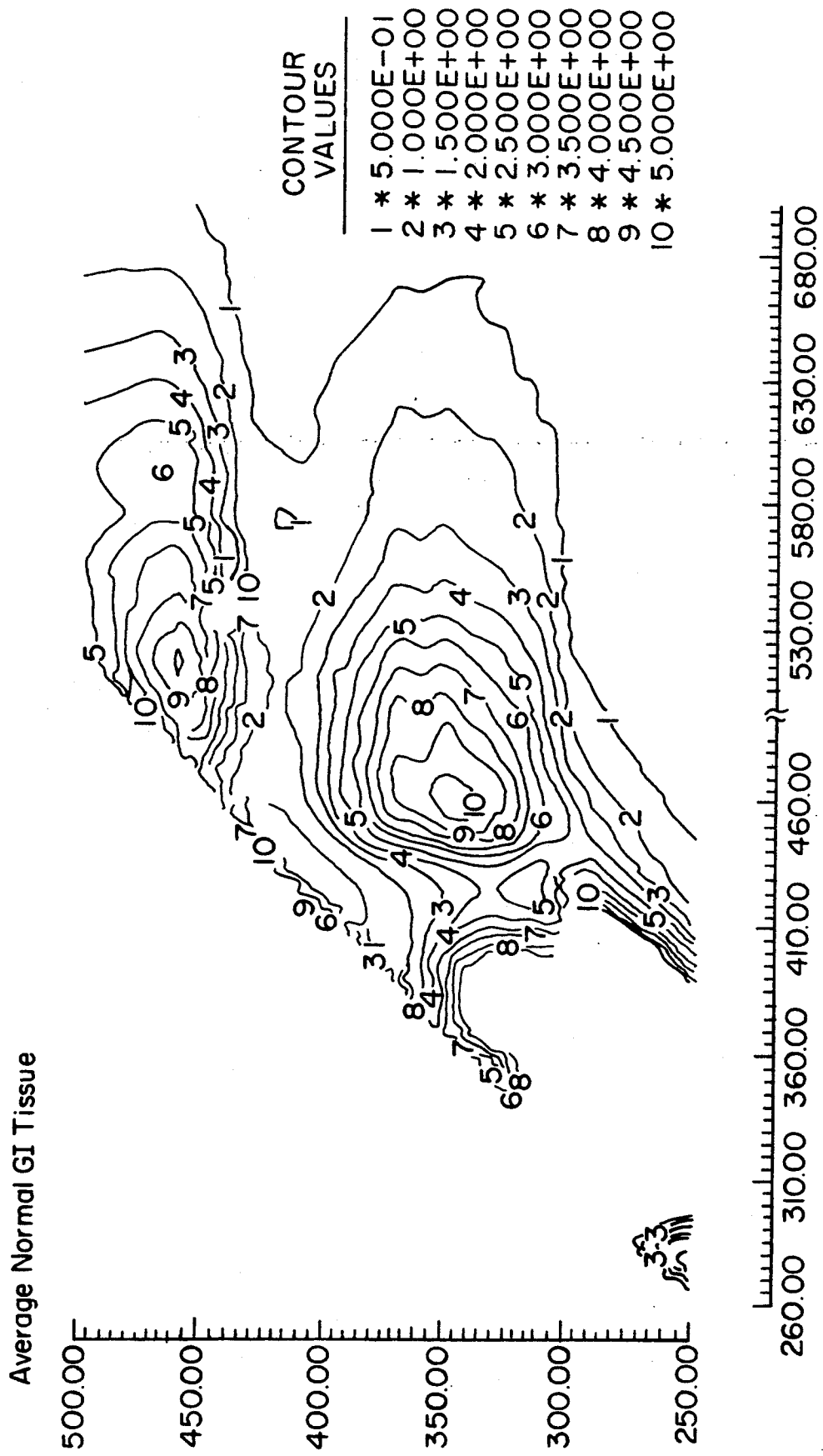
Figure 14A:
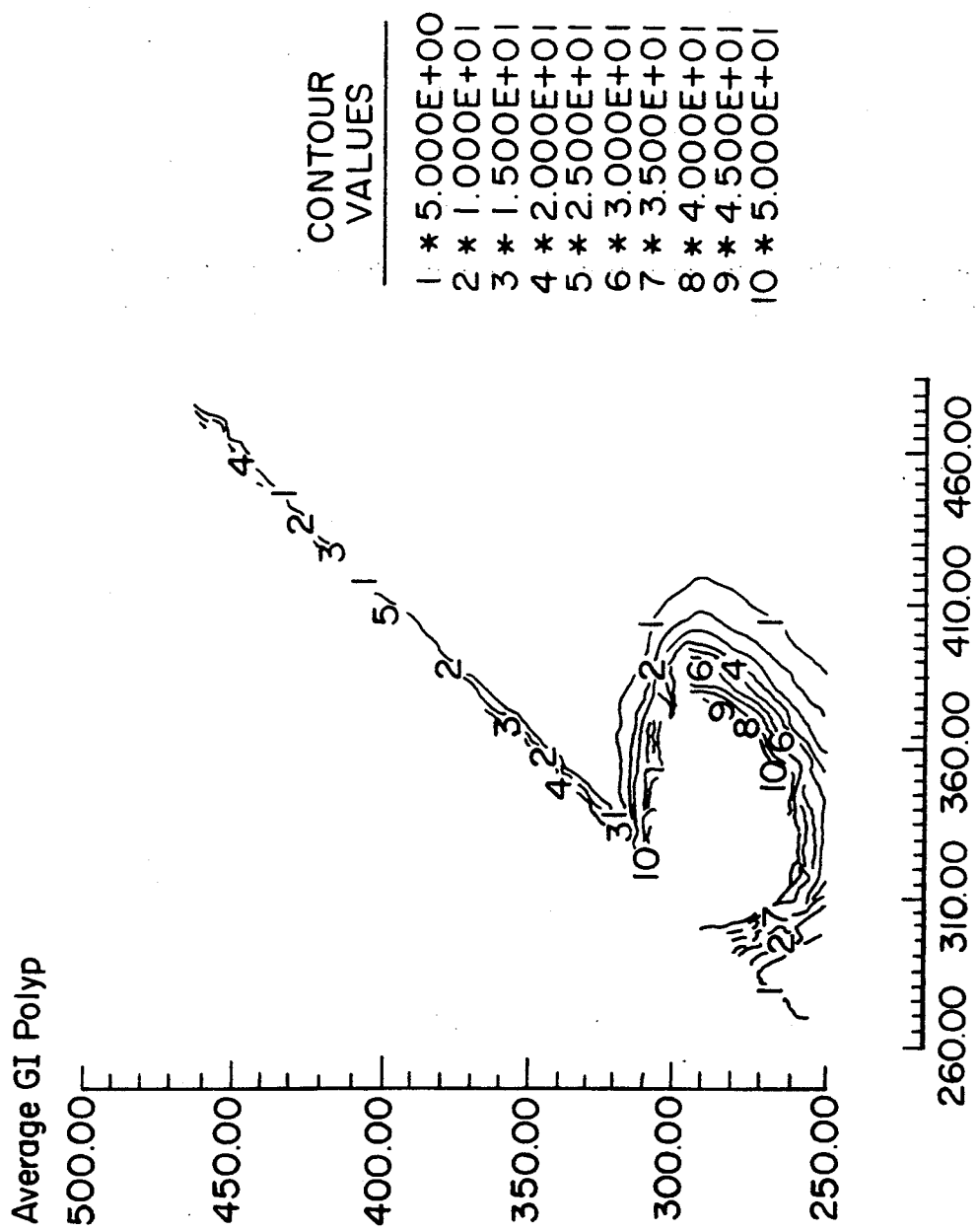
FIGS. 14a and 14b show average fluorescence contour maps for adenomatous human colon tissue.
Figure 14B:
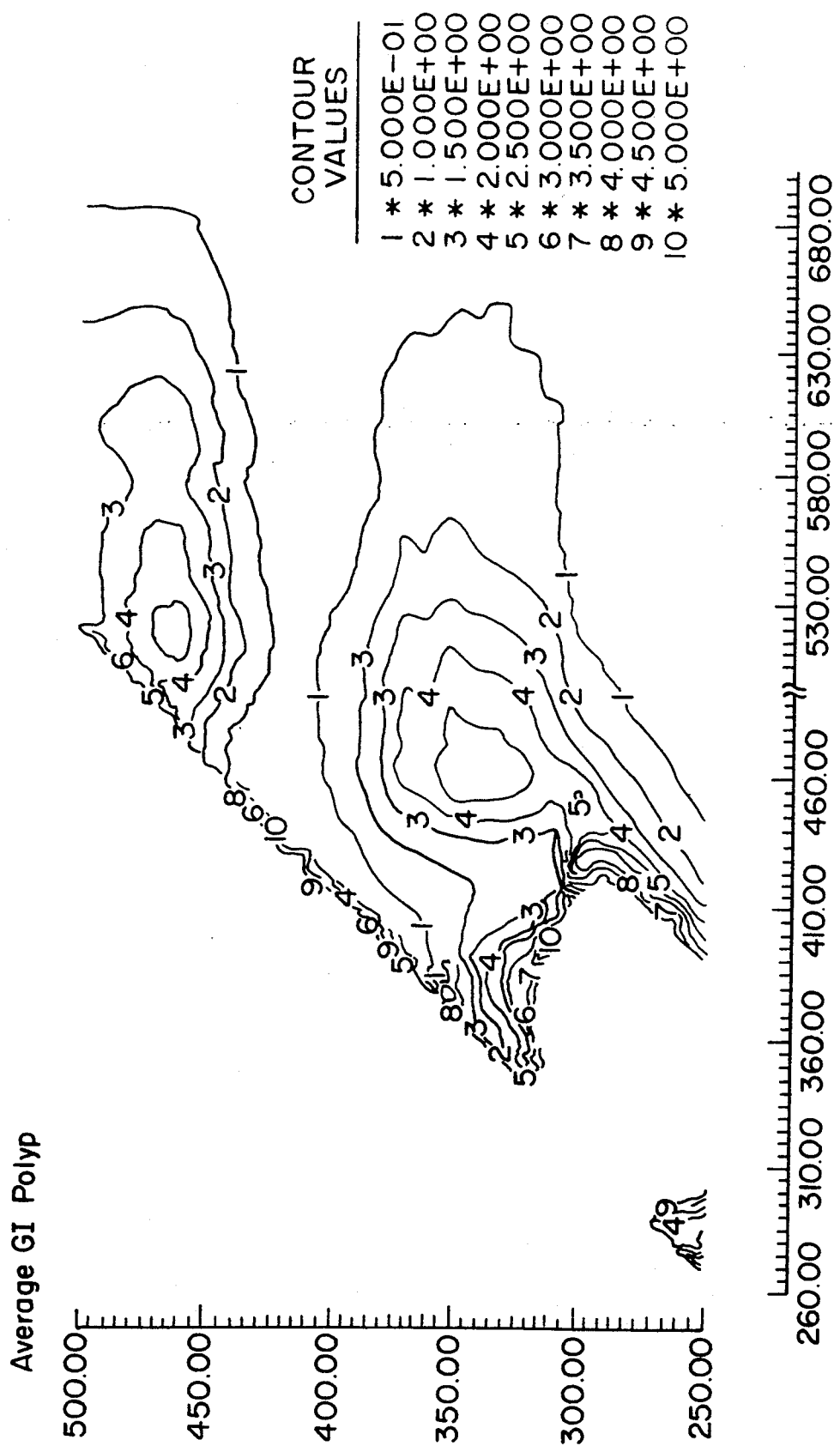

FIGS. 13 and 14 show average fluorescence contour maps of normal and adenomatous human colon tissue. In the normal tissue fluorescence contour map, several major fluorescence and absorption bands can be recognized, as summarized in Table 1. Similarly, Table 2 lists the major absorption and fluorescence bands found in the adenomatous fluorescence contour map.

TABLE 1

Average Normal Colon Tissue

| ($\lambda x$, $\lambda m$) | Fluorescence Intensity | Chromophore |
|---|---|---|
| (285, 340) | 50.0 | Tryptophan |
| (330, 385) | 5.0 | Chromophore Within Collagen |
| (315, 430) | 2.5 | 4-Pyridoxic Acid |
| (345, 465) | 5.0 | NAD(P)H |
| (460, 520) | 4.5 | Flavin |
| ($\lambda$, 420) (420, $\lambda$) ($\lambda$, 540) ($\lambda$, 580) | | Hemoglobin (Heme) |

TABLE 2

Average Adenomatous Colon Tissue

| ($\lambda x$, $\lambda m$) | Fluorescence Intensity | Chromophore |
|---|---|---|
| (285, 340) | 50.0 | Tryptophan |
| (340, 470) | 2.5 | NAD(P)H |
| (460, 520) | 2.5 | Flavin |
| ($\lambda$,420) (420, $\lambda$) ($\lambda$, 540) ($\lambda$, 580) | | Hemoglobin (Heme) |

A comparison of these two tables points out several of the interesting differences in the fluorescence contour maps of normal and adenomatous tissues Both tissues exhibit tryptophan fluorescence. Qualitatively, the shape and peak fluorescence intensity of this band is very similar for both types of tissue Two additional fluorescence bands appear to be present in the normal tissue fluorescence contour map at (330,385) and (315,430). In the visible region of the spectrum, the fluorescence intensity of normal tissues is approximately 2× that of adenomatous tissues. In particular, both tissues show a band near (340,470); this band is 2× higher in normal tissue. In addition, it is more peaked, and slightly shifted in normal tissue relative to adenomatous tissue. Both tissues show a peak at (460,520), which is 1.8× more intense in normal tissue.

Figure 15:
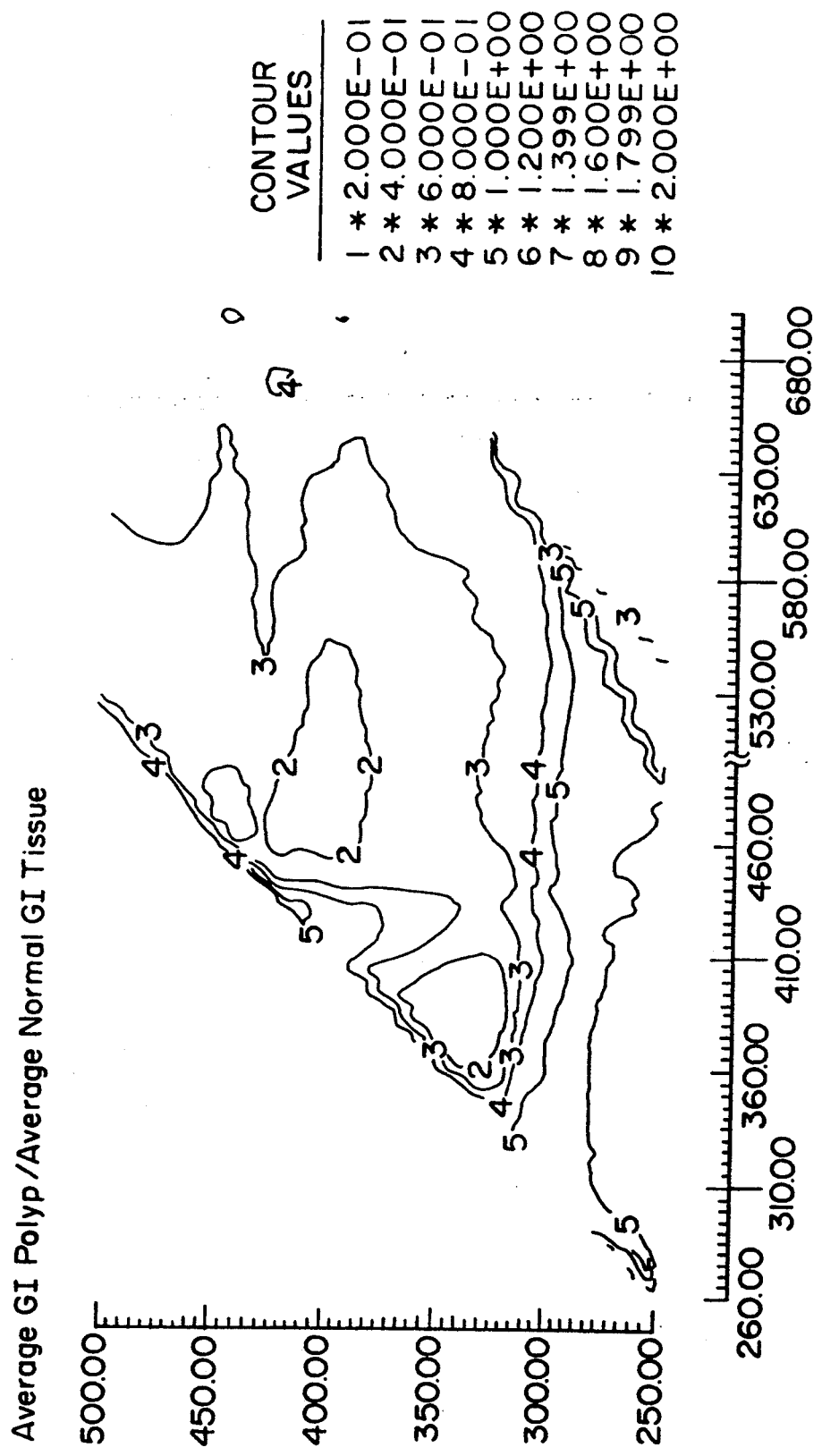
FIG. 15 shows the ratio of an average contour map for adenomatous polyp to an average contour map for normal gastrointestinal tissue.
Figure 16:
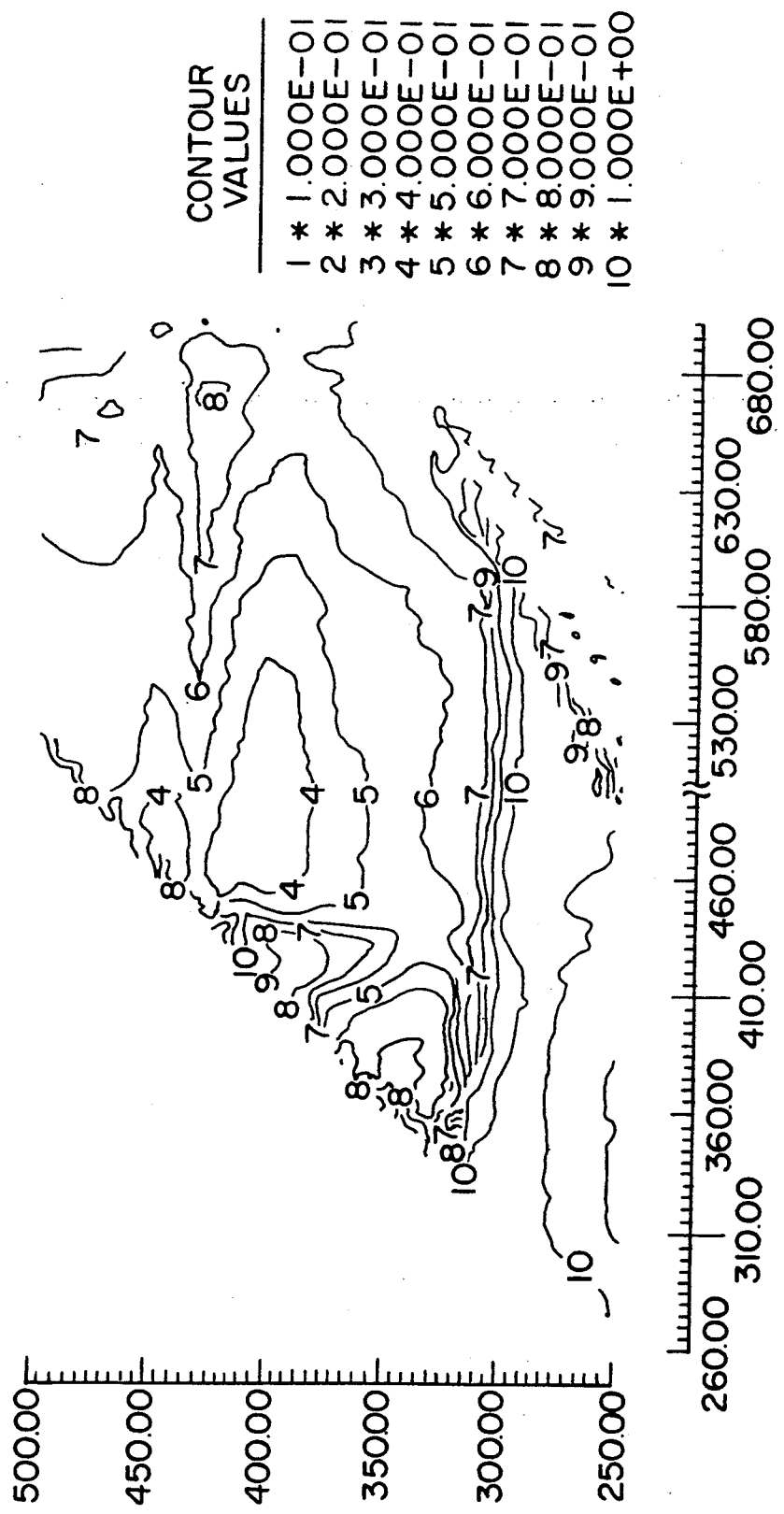
FIG. 16 shows the map of FIG. 15 where the contour line density is increased by a factor of two to show more detail.

These differences are highlighted in FIG. 15, which shows the ratio of the two average contour maps, with contours drawn linearly from 2.0 to 0.2. Greater detail is shown in FIG. 16, with contours drawn from 1.0 to 0.1. Again contours at 1.0 indicate regions where normal and adenomatous tissues exhibit equal fluorescence intensities, while contours greater (less) than 1.0 indicate regions where adenomatous tissue fluorescence is greater (less) than normal tissue fluorescence. In the region of tryptophan fluorescence, a contour with a value of 1.0 is shown, indicating the similarity of tryptophan fluorescence in normal and adenomatous tissues.

A valley is present at (335,385) with a contour level of 0.3 indicating the additional fluorescence band present in normal tissue at this location. A valley is present at (390,430) with a contour of 0.8. Additional valleys are present at (400,495), (440,480), (430,600) and (430,670). These are summarized in Table 3.

TABLE 3

Average Ratio Map, Colon Tissue

| ($\lambda x$, $\lambda m$) | $R_{AVG}(\lambda_x, \lambda_m)$ | Chromophore |
| --- | --- | --- |
| (330, 385) | 0.3 | Chromophore Within Collagen |
| (390, 430) | 0.8 | Pyridoxic Acid Lactone |
| (400, 495) | 0.4 | ? |
| (440, 480) | 0.4 | ? |
| (430, 600) | 0.7 | ? |
| (430, 670) | 0.8 | ? |

Figure 17:
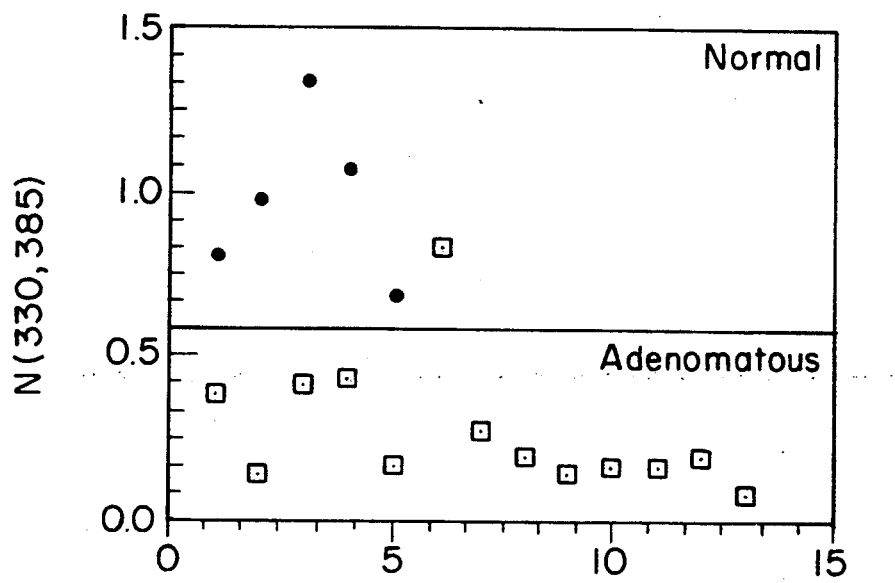
FIG. 17 illustrates a diagnostic algorithm for differentiating adenomatous from normal colon tissue based upon a ratio of maps at an excitation wavelength of 330 nanometers and an emission wavelength of 385 nanometers.
Figure 18:
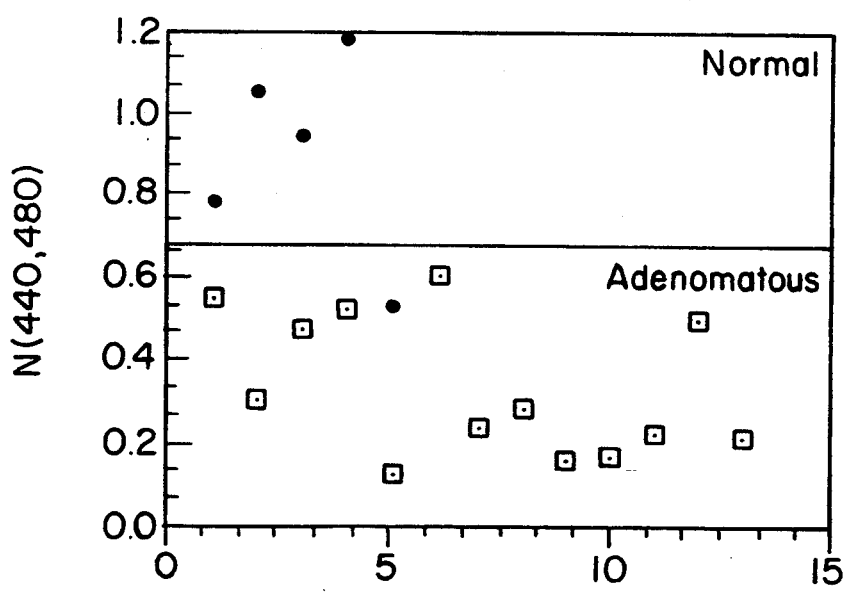
FIG. 18 illustrates a diagnostic algorithm based upon an excitation wavelength of 440 nanometers and an emission wavelength of 480 nanometers.
Figure 19:
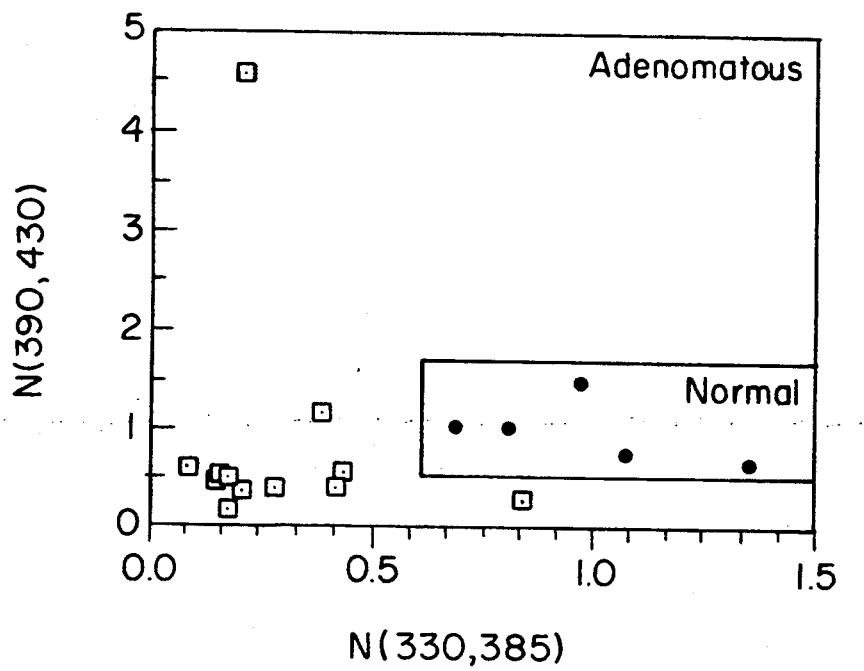
FIG. 19 illustrates a binary type diagnostic algorithm.

The values of the individual ratio maps at these locations of ($\lambda_x, \lambda_m$), can be divided by the intensity of the ratio map at (290,340). Two of these values, at (330,385) and (440,480), independently provided useful diagnostics for differentiating normal and adenomatous tissues (FIGS. 17 and 18). In addition, a binary scheme utilizing information at (390,430) and (330,385) provided an accurate diagnostic process (FIG. 19).

Figure 20A:
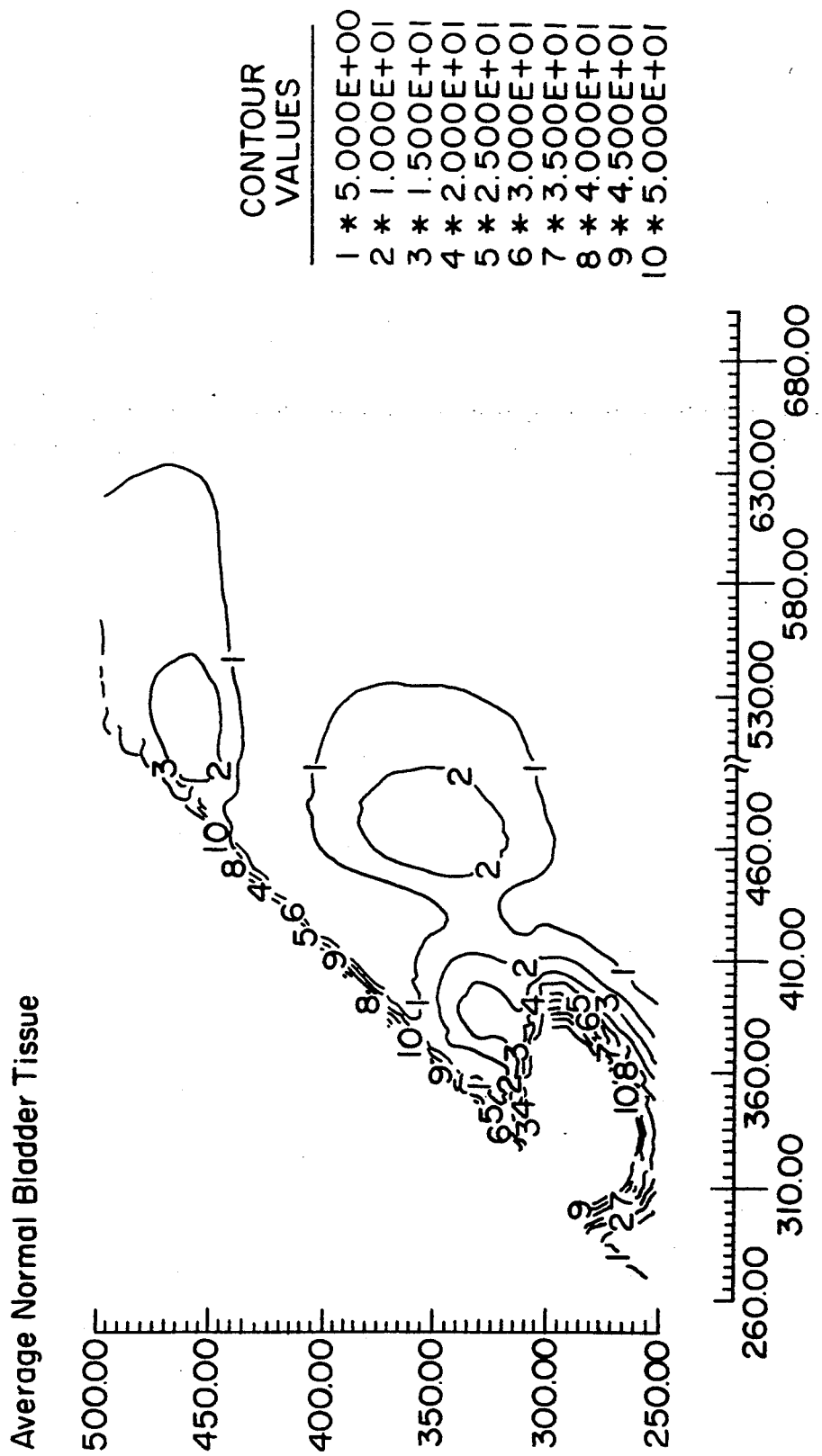
FIGS. 20a and 20b show average contour maps on different scales of normal bladder tissue.
Figure 20B:
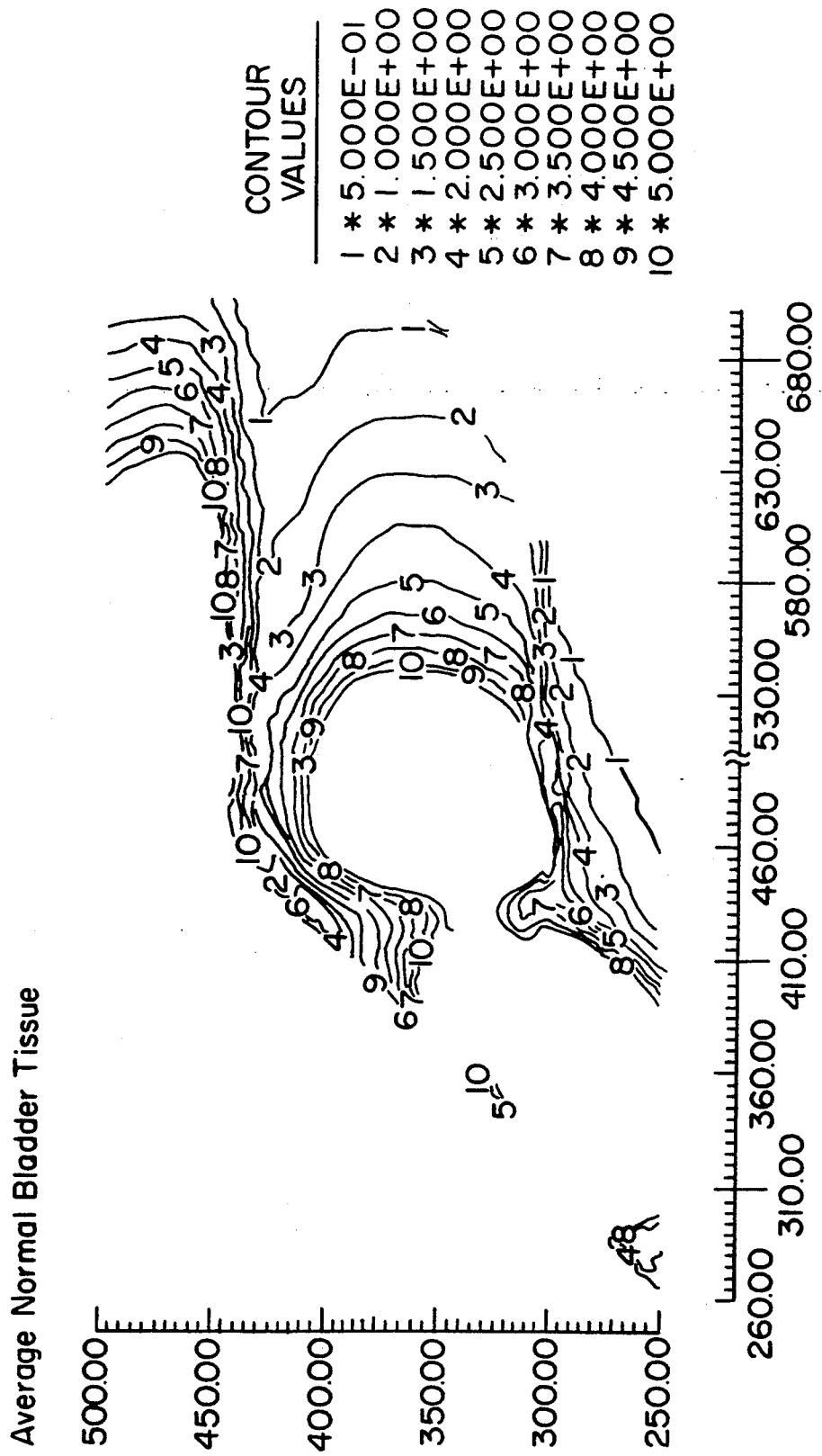
Figure 21A:
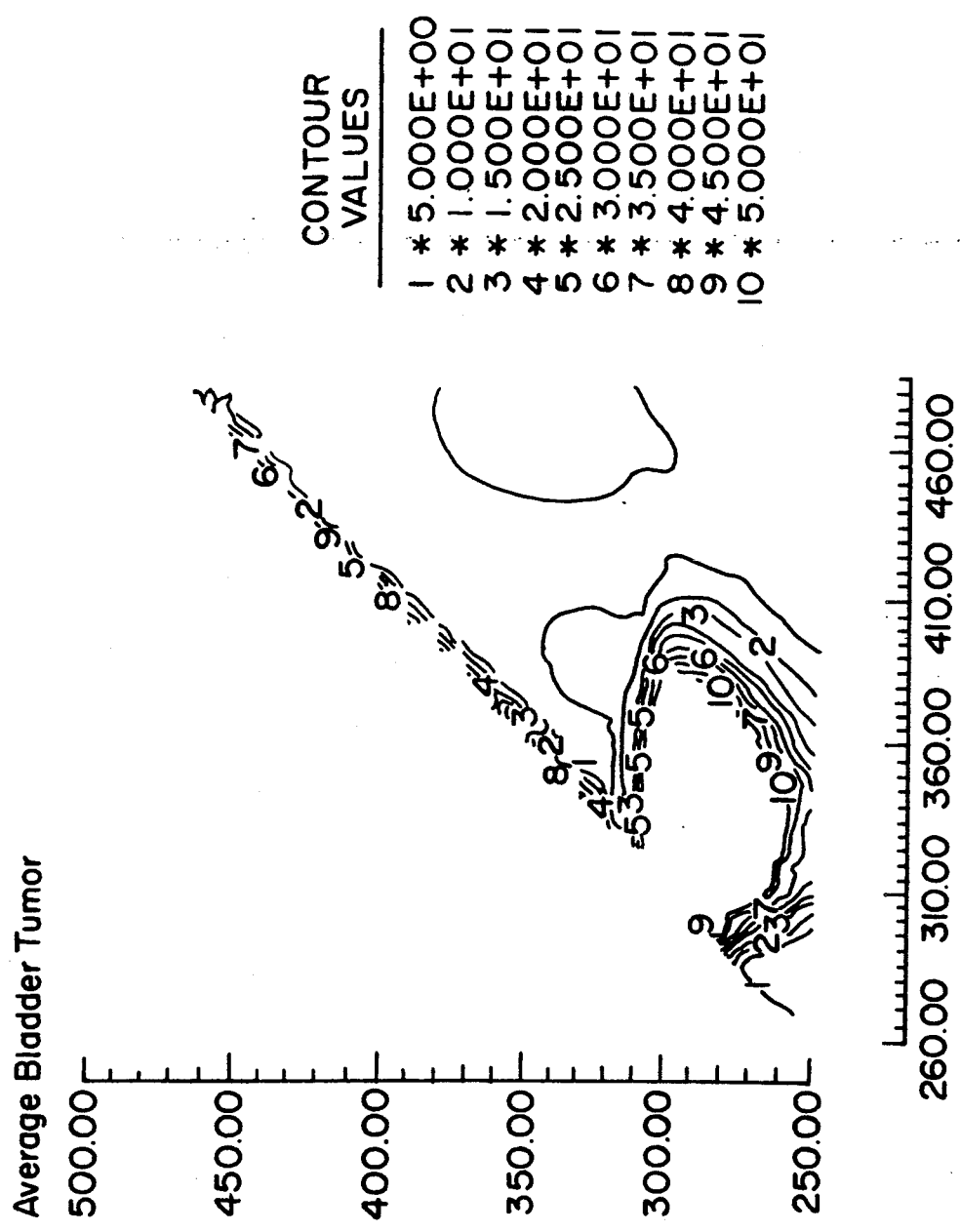
Figure 2L:
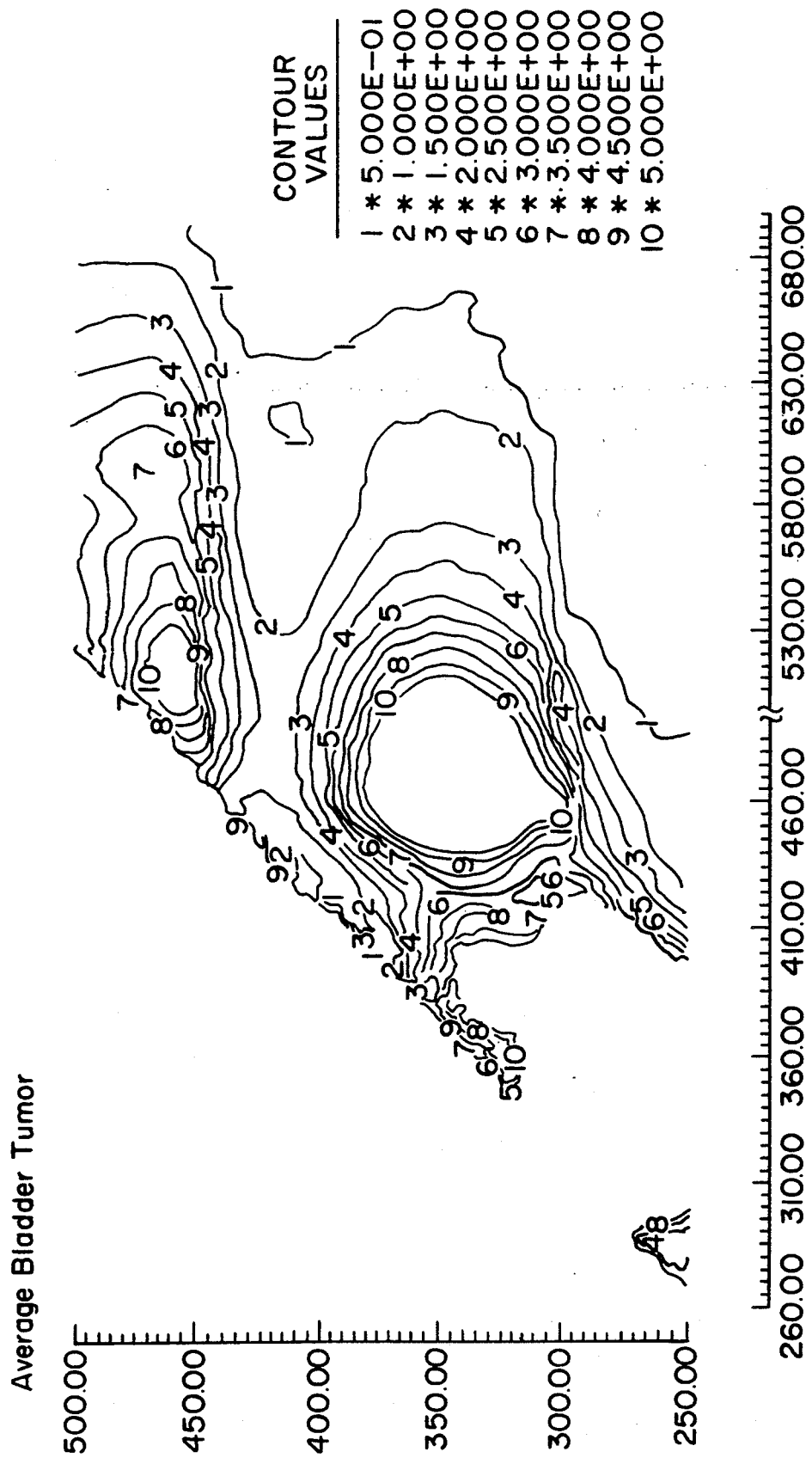

FIGS. 20 and 21 show average fluorescence contour maps of normal bladder wall and tumor. Major fluorescence and absorption bands are summaried in Tables 4 and 5. Again, in the region of tryptophan fluorescence both normal and tumor tissues have similar emission. Although both tissues show a fluorescence band at (325,385), it is 3× stronger in normal tissue. Both tissues show fluorescence peaks at (350,470) with normal tissues exhibiting 2× as much fluorescence intensity. Also at (470,520) the fluorescence of normal tissue is 2× as high as that of tumor tissue. The average tumor map exhibits a unique peak at (315,430).

TABLE 4

Average Normal Bladder Tissue

| ($\lambda x$, $\lambda m$) | Fluorescence Intensity | Chromophore |
| --- | --- | --- |
| (285, 340) | 50.0 | Tryptophan |
| (325, 385) | 15.0 | Chromophore Within Collagen |
| (350, 470) | 10.0 | NAD(P)H |
| (470, 520) | 10.0 | Flavin |
| ($\lambda$, 420) (420, $\lambda$) ($\lambda$, 540) ($\lambda$, 580) | | Hemoglobin (Heme) |

TABLE 5

Average Bladder Tumor

| ($\lambda x$, $\lambda m$) | Fluorescence Intensity | Chromophore |
| --- | --- | --- |
| (285, 340) | 50.0 | Tryptophan |
| (330, 385) | 5.0 | Chromophore Within Collagen |
| (315, 430) | 3.0 | 4-Pyridoxic Acid |
| (350, 470) | 5.0 | NAD(P)H |
| (460, 515) | 5.0 | Flavin |
| ($\lambda$, 420) (420, $\lambda$) ($\lambda$, 540) ($\lambda$, 580) | | Hemoglobin (Heme) |

Figure 24:
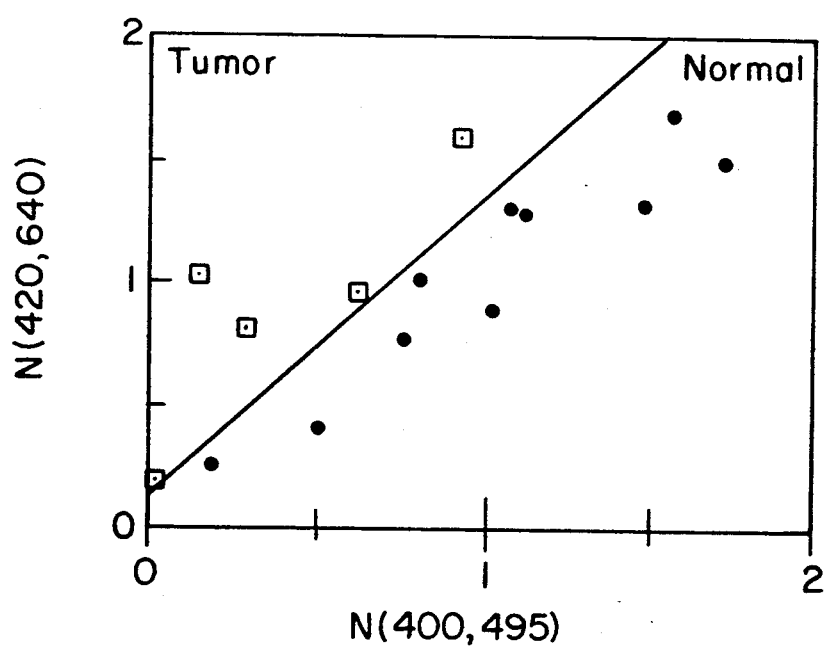
FIG. 24 shows a binary diagnostic algorithm to differentiate bladder tumor from normal bladder tissue.
Figure 22:
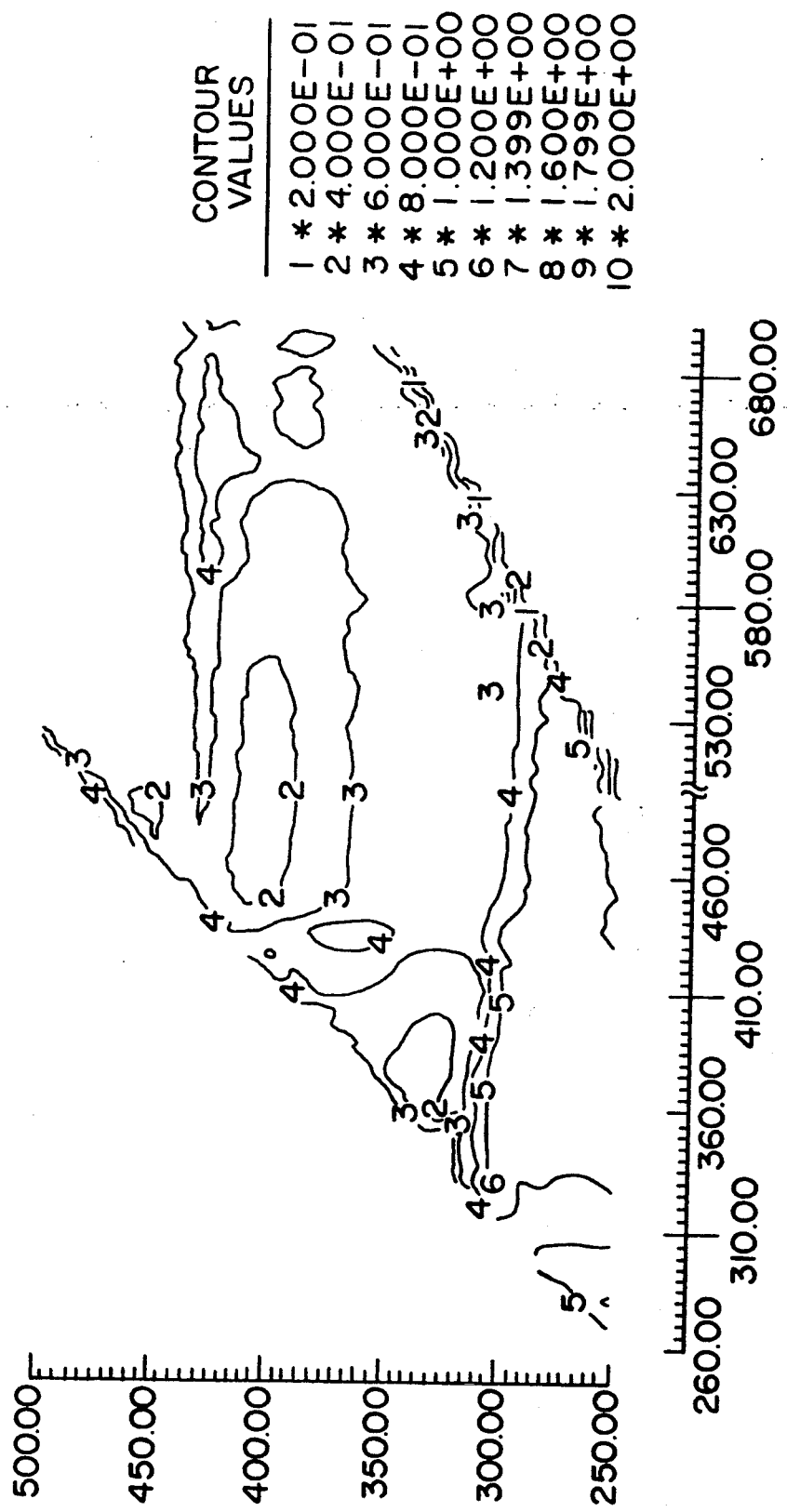
FIG. 22 shows a ratio of contour maps for bladder tumor and normal bladder tissue.
Figure 23:
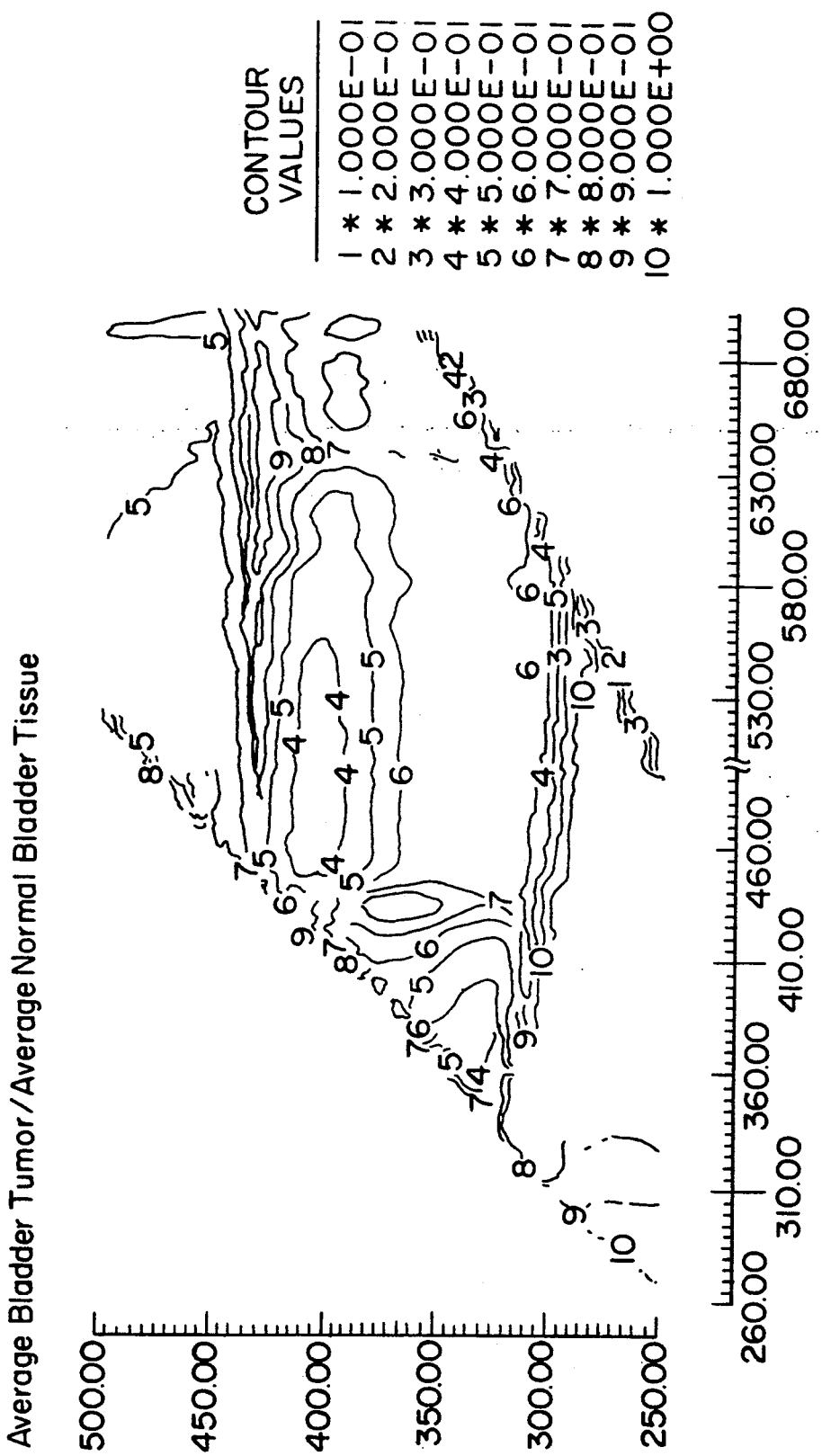
FIG. 23 shows the map of FIG. 22 with a greater contour line density.

These differences are highlighted in FIGS. 22 and 23 which show the ratio contour map of tumor and normal bladder tissue for two sets of contours (2.0–0.2, 1.0–0.1). Table 6 summarizes the valleys present in this ratio map. Valleys are present at (330,385), (370,435), (400,495), (450,485), (420,640), and (390,670). Values of the individual ratio maps at these locations can be divided by the value of the tryptophan peak (290,340). FIG. 24 shows an example of a diagnostic procedure which can be defined from this data.

TABLE 6

Average Ratio Map, Bladder Tissue

| ($\lambda x$, $\lambda m$) | $R_{AVG}(\lambda_x, \lambda_m)$ | Chromophore |
| --- | --- | --- |
| (330, 385) | 0.4 | Chromophore Within Collagen |
| (370, 435) | 0.8 | Pyridoxic Acid Lactone |
| (400, 495) | 0.5 | ? |
| (450, 485) | 0.4 | ? |
| (420, 640) | 0.9 | ? |
| (390, 670) | 0.6 | ? |

Because of the voluminous information in the 2-D plots, a model is useful in interpreting the data. Even if the types and concentrations of all chromophores were known, quenching, spectral shifts, and energy transfer due to the local environment would alter a calculated spectrum. But, in spite of these many unknowns, a "landscape" model of chromophore behavior does provide some general insights for locating distinctive features for comparative spectral diagnosis.

The model begins with the reasonable assumption that tissue contains a few relatively strongly fluorescing chromophores, a background of weaker ones, and absorbers which are probably non-fluorescent. The strong chromophores, with relatively high quantum yields or concentrations (or both), will generate "peaks" on the contour plot. In addition, these chromophores generally have a broad base which tends toward shorter wavelengths for excitation; and due to the general anharmonicity of higher vibrational levels, it tends toward longer wavelengths for emission. Combining with the weaker chromophores, this forms an average elevation of signal background from which the peaks arise. The absorbers cut vertically and horizontally across the spectral terrain. The percent decrease along the line should be approximately constant to the extent that the penetration depth is constant. This is distinguishable from a "pass" between two spectral peaks, which is just lesser fluorescence, not absorption. Thin sections will be quite helpful in identifying absorption features by their absence.

Distinguishing diseased vs. healthy tissue is essentially distinguishing one set of chromophore signals from another. If two tissues have different amounts of one chromophore, then the corresponding absolute signals might be measured; however, this is dependent on collection geometry. Comparisons, or ratios, are less geometry dependent, but appropriate positions on the 2-D surface need to be selected. The data is normalized so as to again avoid geometry-dependent ratios.

The spectral landscape model has three regions: 1) fluorescent peaks, 2) an average elevation, or plateau, and 3) absorption valleys. Of these, region 1 is the most appealing as a discriminant for tissue type, as it would show a characteristic chromophore. Region 3 is susceptible to variability or leaching as has been shown for the case of heme, and region 2, being comprised of fluorescence from several chromophores, is likely to have the least variation overall. Signal change due to a change in one of the chromophores would be diminished by the fraction of the total signal contributed by that chromophore. In other words, instead of comparing absolute peak heights, they should first be normalized relative to the average elevation. Ideally, normalization would be relative to selected regions thought to be "average"; a practical compromise is the average height from the total integrated signal of the entire plot. Peaks then have signals >1, and valleys generally <1. The comparison signal $R\lambda$ for each set of excitation and emission wavelengths, equals the diseased signal $D\lambda$, divided by the normal tissue signal, $N\lambda$.

$$R\lambda = D\lambda/N\lambda$$

If subtraction is used instead of the ratio, then this number should be normalized to the signal strength at that wavelength to indicate the fractional, rather than absolute, change:

$$S\lambda = \Delta D\lambda/N\lambda,$$

where $\Delta D\lambda = D\lambda - N\lambda$ and therefore $S\lambda = R\lambda - 1$.

This gives the normalized differential signal $S\lambda$. N is in the denominator, since it is desirable to determine the deviation of the diseased tissue from normal. When the "peak" value is selected, it should be integrated over the top 10%–20% of the peak, thereby incorporating a substantial volume of the fluorescence signal; otherwise, data is discarded, and the noise level is increased.

An alternative approach is to normalize two contour plots to the same chromophore peak, then ratio them. This would compare amplitudes of other peaks to the first. However, the ratioed contour plot is dependent on which peak is selected for normalization, and the information from the rest of the plot, which provides the total integrated signal, is in effect, unused.

Additional information is contained in the peak shape. If the different environments of the tissue cause spectral shifts, then this may be emphasized by ratioing normalized peaks on two contour plots. In this case a smaller integrated area may be better for normalization. Deviations from unity will indicate different slopes or shapes.

To avoid overemphasizing weaker parts of the spectrum, a weighting factor may be introduced: Assuming that the signal to noise ratio varies as the square root of the signal, the ratio signal should be multiplied by the square root of $N\lambda$ to yield $W\lambda$, the weighted normalized ratio contour plot comparing the two tissue types.

$$W\lambda = N\lambda R\lambda.$$

These computations should be straightforward for numerical peak comparison. Large differences in regions where the fluorescence is weak will be de-emphasized.

We claim:

1. A method of processing spectra generated from the induced fluorescence of tissue comprising:

irradiating a portion of tissue over a range of periodically separated excitation wavelengths with radiation from a light source to induce autofluorescence of the tissue such that the tissue emits fluorescent radiation at a multiplicity of emission wavelengths;

forming a spectrum of the intensity of the emitted radiation from the recorded fluorescing radiation at each of the multiplicity of excitation and emission wavelengths;

repeating the irradiating and forming steps to provide a plurality of spectra;

averaging the plurality of spectra to produce an average spectrum; and identifying fluorophores present in the tissue that have predetermined fluorescence characteristics which correlate with spectral features in the average spectrum, the feature having identified excitation and emission wavelengths present in the average spectrum.

2. The method of processing spectra of claim 1 wherein the tissue comprises arterial tissue.

3. The method of processing spectra of claim 1 wherein the tissue comprises colon tissue.

4. The method of processing spectra of claim 1 wherein the tissue comprises bladder tissue.

5. The method of processing spectra of claim 1 further comprising the step of forming a difference spectra by taking the difference between the formed spectrum and a reference spectrum.

6. The method of processing spectra of claim 1 further comprising identifying a region within the spectrum wherein the intensity in the region is reduced by a component of tissue which absorbs radiation.

7. The method of processing spectra of claim 6 further comprising adjusting the intensity in the region to correct for a contribution to the spectrum by the absorbing component of tissue.

8. The method of processing spectra of claim 1 further comprising the step of forming a ratio spectrum by dividing the formed spectrum by a reference spectrum.

9. A method of diagnosing bodily tissue comprising:

inserting a catheter containing an optical fiber into a body lumen and positioning a distal end of the catheter adjacent to tissue to be diagnosed;

coupling a proximal end of the catheter to a radiation source such that the radiation is transmitted along the optical fiber and directed onto the tissue to be diagnosed;

inducting autofluorescence with the tissue with the radiation source with a multiplicity of periodically separated excitation wavelengths;

recording the autofluorescent radiation emitted by the tissue at a multiplicity of emission wavelengths;

forming a spectral matrix of the intensity of the emitted radiation from the recorded radiation at each of the multiplicity of excitation and emission wavelengths;

repeating the inducing and recording steps to provide a plurality of the spectral matrices;

averaging the plurality of spectral matrix to produce an average spectral matrices; and identifying fluorophores present in the tissue from the average spectral matrix to diagnose a condition of the tissue.

10. The method of claim 9 further comprising comparing the spectral matrix with a reference matrix to determine the presence of abnormal tissue.

11. The method of claim 9 wherein the radiation source comprises a laser.

12. The method of claim 9 wherein the lumen comprises an artery such that fluorophores of atherosclerotic material within the artery are identified.

13. The method of claim 9 further comprising identifying a portion of the spectral matrix wherein the intensity of the emitted radiation is reduced by a component of tissue which absorbs radiation.

14. The method of claim 13 further comprising adjusting the intensity of the identified portion of the spectral matrix to correct for the reduced intensity.

15. A method of diagnosing vascular tissue comprising:
- inserting a catheter containing an optical fiber into a vascular lumen and positioning a distal end of the catheter adjacent to vascular tissue to be diagnosed;
- coupling a proximal end of the catheter to a laser radiation source such that the laser radiation is transmitted along the optical fiber and directed onto the tissue to be diagnosed;
- inducing inelastically scattered light to be emitted from the vascular tissue with the laser radiation with a multiplicity of periodically separated excitation wavelengths;
- recording the scattered radiation returning from the tissue at a multiplicity of emission wavelengths;
- forming a spectral matrix of the intensity of the emitted radiation from the recorded radiation at each of the multiplicity of excitation and emission wavelengths;
- repeating the inducing and recording steps to provide a plurality of spectral matrices;
- averaging the spectral matrices to provide an average spectral matrix; and
- identifying abnormal tissue present in the tissue from the average spectral matrix.

16. The method of claim 15 further comprising comparing the spectral matrix with a reference matrix to determine the presence of abnormal tissue.

17. The method of claim 15 wherein the lumen comprises an artery such that fluorophores of atherosclerotic material within the artery are identified.

18. The method of claim 15 further comprising identifying a portion of the spectral matrix wherein the intensity of the emitted radiation is reduced by a component of tissue which absorbs radiation.

19. The method of claim 18 further comprising adjusting the intensity of the identified portion of the spectral matrix to correct for the reduced intensity.

20. The method of claim 15 wherein the inelastically scattered light comprises fluorescence.

* * * * *